US011175296B2

(12) United States Patent
Van Tine et al.

(10) Patent No.: US 11,175,296 B2
(45) Date of Patent: Nov. 16, 2021

(54) METHODS OF DIAGNOSING AND TREATING CANCER COMPRISING ME1

(71) Applicants: Brian Van Tine, St. Louis, MO (US); Sara S. Lange, St. Louis, MO (US); Jeff Kremer, St. Louis, MO (US)

(72) Inventors: Brian Van Tine, St. Louis, MO (US); Sara S. Lange, St. Louis, MO (US); Jeff Kremer, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/794,386

(22) Filed: Oct. 26, 2017

(65) Prior Publication Data

US 2018/0120336 A1 May 3, 2018

Related U.S. Application Data

(60) Provisional application No. 62/413,238, filed on Oct. 26, 2016.

(51) Int. Cl.

| | |
|---|---|
| *G01N 33/92* | (2006.01) |
| *G01N 33/50* | (2006.01) |
| *A61K 31/496* | (2006.01) |
| *A61K 45/06* | (2006.01) |
| *A61P 35/00* | (2006.01) |
| *A61K 31/167* | (2006.01) |
| *A61K 31/635* | (2006.01) |
| *A61K 31/40* | (2006.01) |
| *A61K 31/517* | (2006.01) |
| *A61K 31/198* | (2006.01) |
| *A61K 31/357* | (2006.01) |
| *G01N 33/574* | (2006.01) |
| *A61K 31/44* | (2006.01) |

(52) U.S. Cl.
CPC .......... *G01N 33/92* (2013.01); *A61K 31/167* (2013.01); *A61K 31/198* (2013.01); *A61K 31/357* (2013.01); *A61K 31/40* (2013.01); *A61K 31/44* (2013.01); *A61K 31/496* (2013.01); *A61K 31/517* (2013.01); *A61K 31/635* (2013.01); *A61K 45/06* (2013.01); *A61P 35/00* (2018.01); *G01N 33/5091* (2013.01); *G01N 33/57407* (2013.01); *G01N 2333/775* (2013.01); *G01N 2333/902* (2013.01); *G01N 2333/90209* (2013.01); *G01N 2800/044* (2013.01); *G01N 2800/50* (2013.01); *G01N 2800/52* (2013.01); *G01N 2800/56* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 6,566,495 B1 | 5/2003 | Fodor et al. | |
| 7,939,313 B2 | 5/2011 | Heyduk et al. | |
| 2015/0110773 A1* | 4/2015 | Kimmelman | C12Q 1/34 424/130.1 |
| 2017/0015660 A1* | 1/2017 | Hawkins | C07D 451/14 |

FOREIGN PATENT DOCUMENTS

WO 2015153814 A1 10/2015

OTHER PUBLICATIONS

Enard et al. (Science 2002 vol. 296 p. 340) (Year: 2002).*
Cobb et al (Crit Care Med 2002 vol. 30 p. 2711) (Year: 2002).*
Bucknall, M. et al., "Practical Quantitative Biomedical Applications of MALDI-TOF Mass Spectrometry," J. Am. Soc. Mass Spectrom., 2002, pp. 1015-1027, vol. 13, Elsevier Science Inc.
Chen, Q. et al., "Apo2L/TRAIL and Bcl-2-related proteins regulate type I interferon-induced apoptosis in multiple myeloma," Blood, Oct. 1, 2001, pp. 2183-2192, vol. 98, No. 7.
Dos Santos, N. et al., "Molecular Mechanisms Underlying Human Synovial Sarcoma Development," Genes, Chromosomes Cancer, Jan. 2001, pp. 1-14, vol. 30, No. 1.
Eilber, F. et al., "Diagnosis and Management of Synovial Sarcoma," J. Surg. Onc., 2008, pp. 314-320, vol. 97, Wiley-Liss, Inc.
Ferrari, A. et al., "Synovial Sarcoma: A Retrospective Analysis of 271 Patients of All Ages Treated at a Single Institution," Cancer, 2004, pp. 627-634, vol. 101.
Feun, L. et al., "Negative argininosuccinate synthetase expression in melanoma tumours may predict clinical benefit from arginine-depleting therapy with pegylated arginine deiminase," Br. J. Can., 2012, pp. 1481-1485, vol. 106, Nature Publishing Group.
Gobom, J. et al., "Detection and Quantification of Neurotensin in Human Brain Tissue by Matrix-Assisted Laser Desorption/Ionization Time-of-Flight Mass Spectrometry," Anal. Chem., Jul. 5, 2000, pp. 3320-3326, vol. 72, No. 14.
Ladanyi, M., "Fusions of the SYT and SSX genes in synovial sarcoma," Oncogene, Sep. 10, 2001, pp. 5755-5762, vol. 20, No. 40, Nature Publishing Group.
Manz, D. et al., "Iron and cancer: recent insights," Ann N.Y. Acad. Sci., 2016, pp. 1-13.
Mirgorodskaya, E. et al., "Characterization of Protein Glycosylation by MALDI-TOFMS," Methods Mol. Biol., 2000, pp. 273-292, vol. 146, Humana Press Inc.
Noguchi, Y. et al., "Tumor-Induced Alterations in Hepatic Malic Enzyme and Carnitine Palmitoyltransferase Activity," J. Surg. Res., 1993, pp. 357-363, vol. 55, Academic Press, Inc.
Rockett, J. et al., "DNA arrays: technology, options and toxicological applications," Xenobiotica, 2000, pp. 155-177, vol. 30, No. 2, Taylor & Francis Ltd.
Sandberg, A. et al., "Updates on the cytogenetics and molecular genetics of bone and soft tissue tumors. Synovial sarcoma," Cancer Genet. Cytogenet., Feb. 2002, pp. 1-23, vol. 133, No. 1, Elsevier.

(Continued)

*Primary Examiner* — Katherine D Salmon
(74) *Attorney, Agent, or Firm* — Polsinelli PC

(57) ABSTRACT

The present disclosure provides a method of determining treatment for cancer comprising identifying the absence of malic enzyme 1 (ME1) and treating with an inducer of ferroptosis.

13 Claims, 31 Drawing Sheets

Specification includes a Sequence Listing.

(56) References Cited

OTHER PUBLICATIONS

Van Tine, B., "Targeting the Pentose Phosphate Pathway for the Treatment of Synovial Sarcoma," Sarcoma Foundation of America, Aug. 25, 2014, 2 pgs., abstract only.
Xie, Y. et al., "Ferroptosis: process and function," Cell Death and Differentiation, 2016, pp. 369-379, vol. 23, Macmillan Publishers Limited.
Yang, L. et al., "Molecular cloning of ESET, a novel histone H3-specific methyltransferase that interacts with ERG transcription factor," Oncogene, 2002, pp. 148-152, vol. 21, Nature Publishing Group.

* cited by examiner

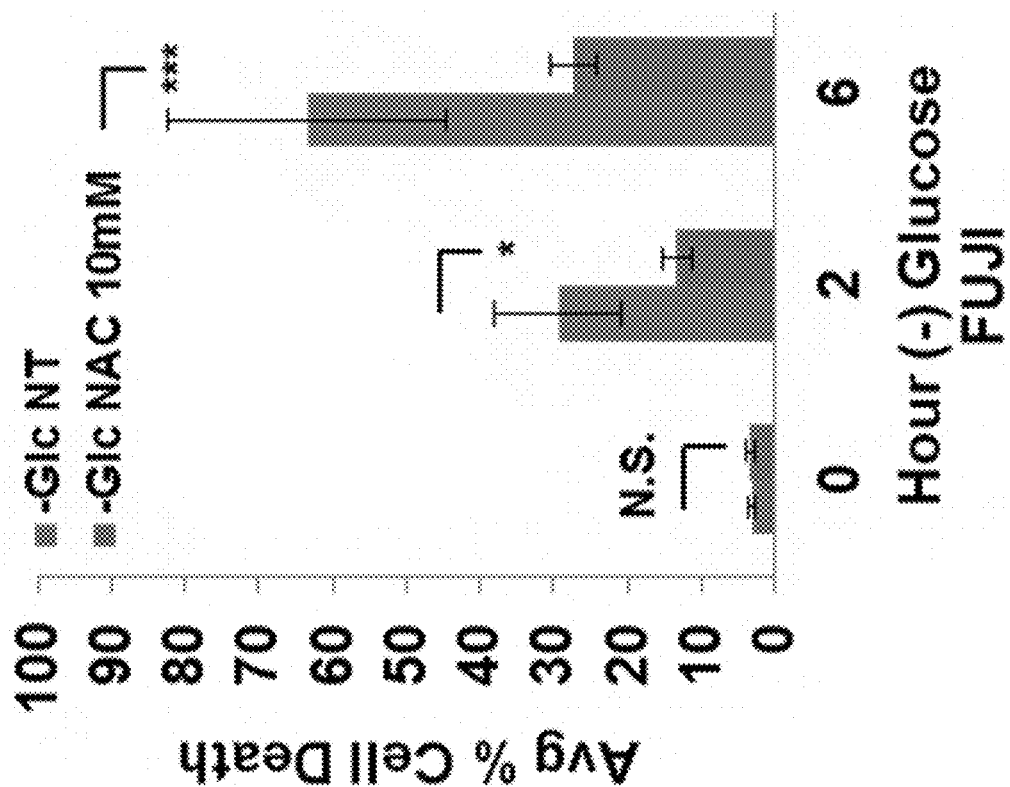
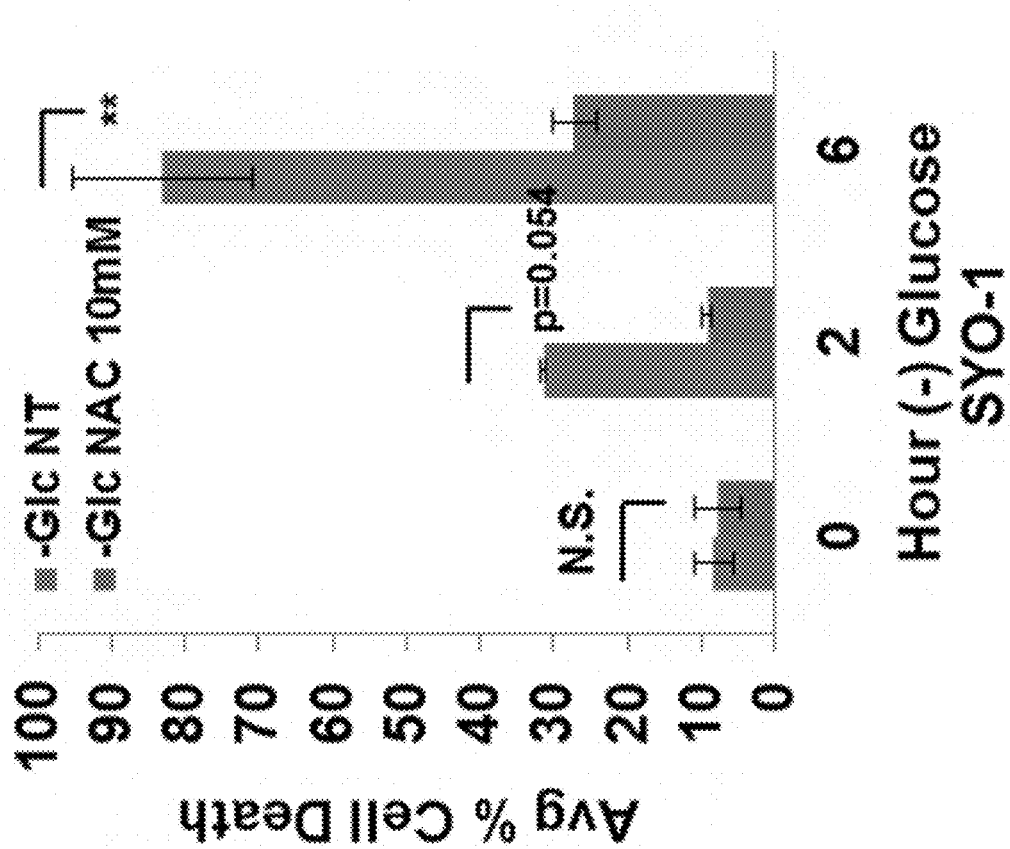
FIG. 5A
FIG. 5B

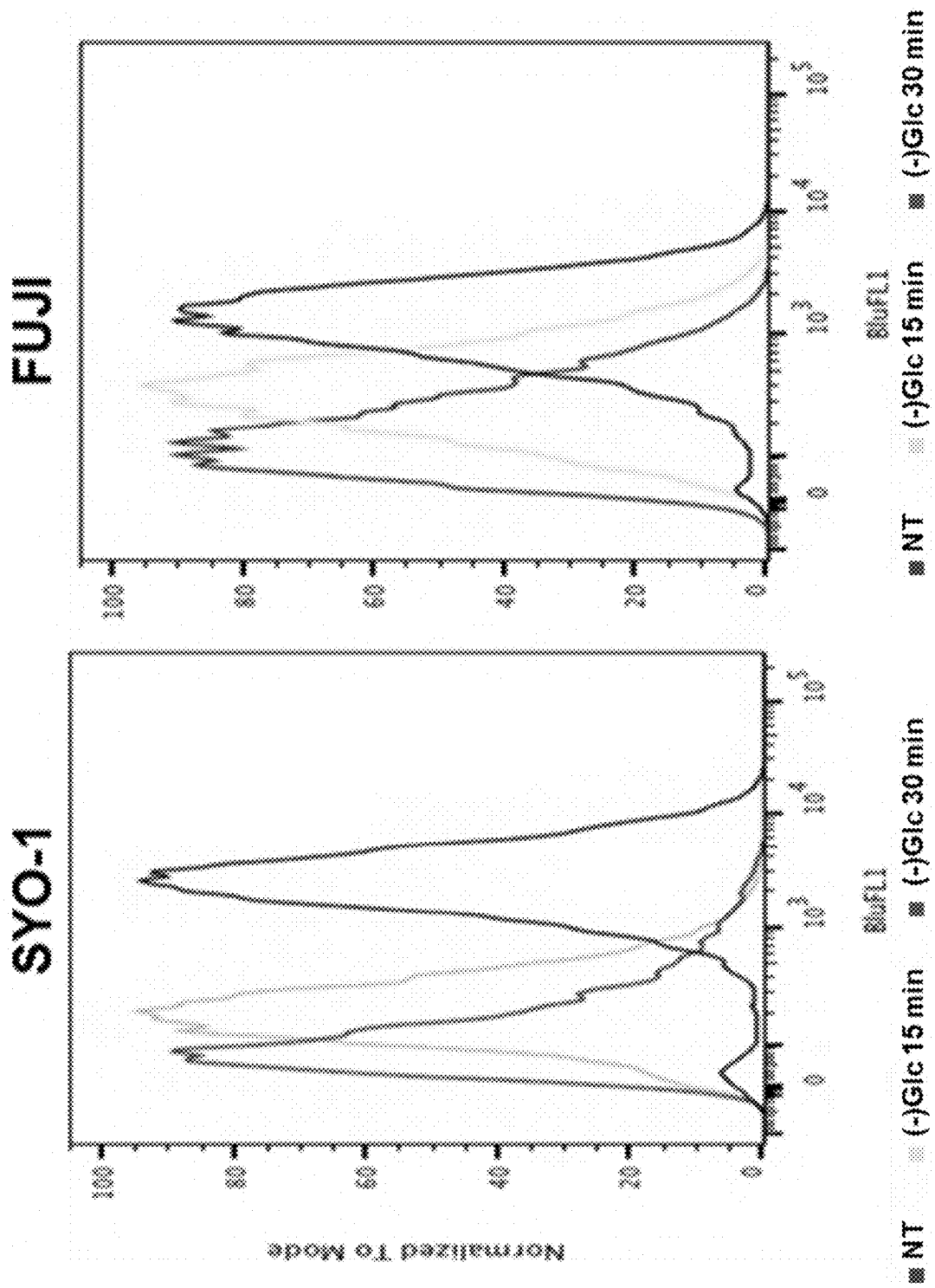

|  | Negative | Starry Sky Pattern | Positive |
| --- | --- | --- | --- |
| Leiomyosarcoma | 0 | 0 | 20 |
| Synovial Sarcoma Human | | | |
| Monophasic | 5 | 8 | 0 |
| Biphasic Sarcomatous | 7 | 0 | 0 |
| Biphasic Carcinomatous | 0 | 0 | 7 |
| Synovial Sarcoma Mouse | | | |
| Monophasic | | | |
| Biphasic | | | |

FIG. 10G

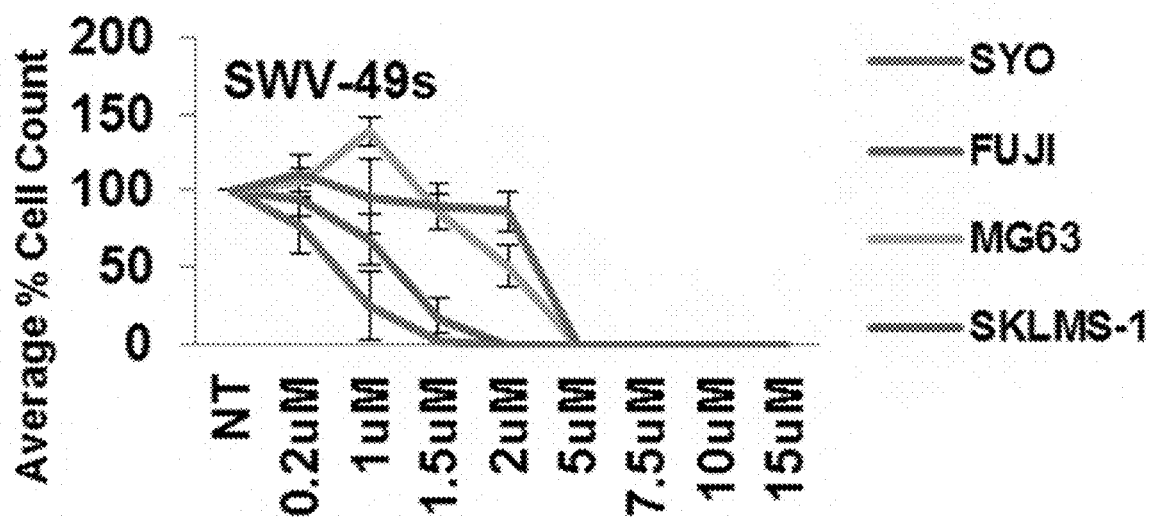
FIG. 12C
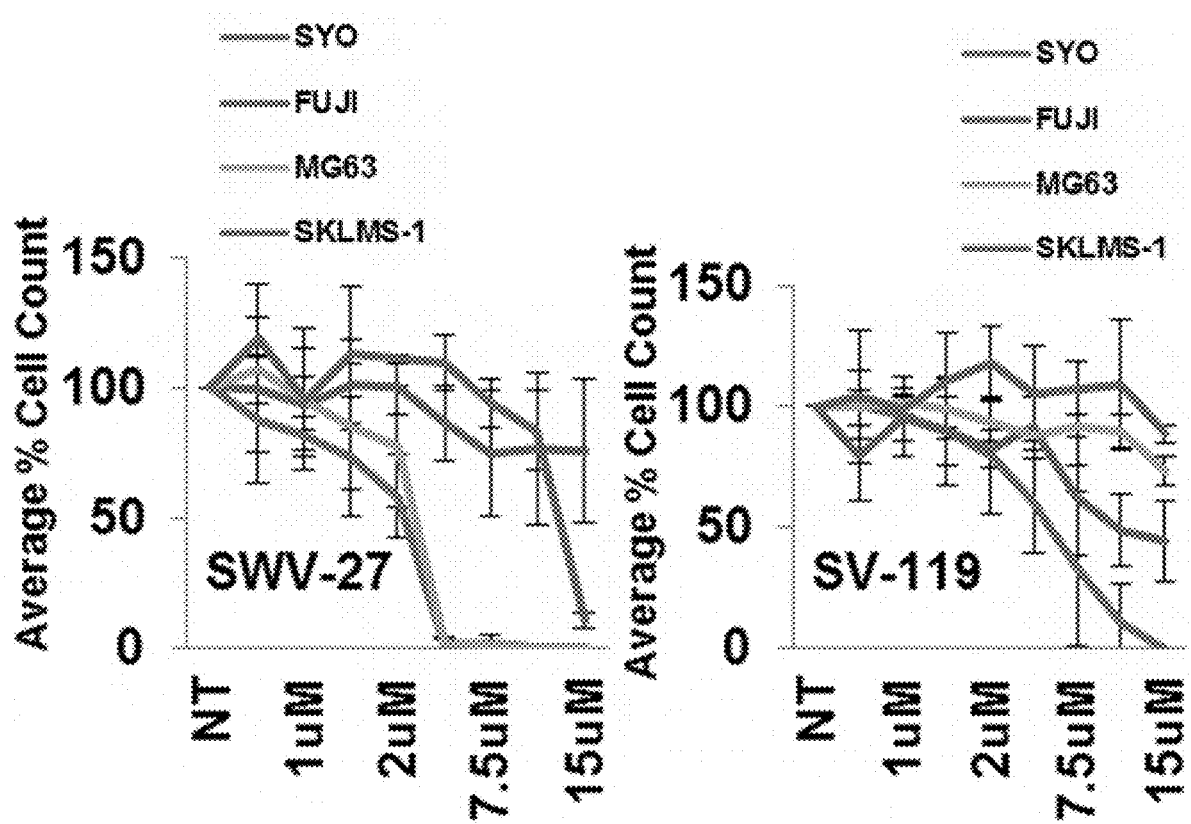
FIG. 12D  FIG. 12E

METHODS OF DIAGNOSING AND TREATING CANCER COMPRISING ME1

CROSS REFERENCE TO RELATED APPLICATIONS

This application claims the priority of U.S. provisional application No. 62/413,238, filed Oct. 26, 2016, hereby incorporated by reference in its entirety.

FIELD OF THE INVENTION

The present disclosure provides a method of determining treatment for cancer comprising identifying the absence of malic enzyme 1 (ME1) and treating with an inducer of ferroptosis.

BACKGROUND OF THE INVENTION

Synovial sarcoma (SS) is a rare and aggressive form of soft tissue sarcoma (STS) with a high metastatic potential. The incidence of SS is estimated at 900-1000 cases per year and accounts for 8-10% of all STS diagnoses in the United States. SS is typically diagnosed in young people between the ages of fifteen and forty. Although SS can develop at any anatomic site, it frequently develops as a soft tissue mass in the extremity in approximately 80% of cases. Despite its name, SS rarely involve the actual joint and are not associated with synovial tissue. It has been difficult to draw clear conclusions regarding the prognostic factors, treatment outcomes, and survival statistics of SS in adults given the general rarity of the disease. Although SS is viewed as moderately sensitive to cytotoxic chemotherapy, once metastatic it can result in late recurrence that leads to a poor long-term overall survival. Currently, the 5-year distant recurrence rate, 5-year survival rate, and 10-year survival rate is 39%, 60%, and 34% respectively. To date, there is not a targeted therapeutic approach for the treatment of primary or metastatic SS. Thus there is a need in the art for a means of determining treatment strategy for SS.

SUMMARY OF THE INVENTION

In an aspect, the disclosure provides a method to classify a subject based on the amount of ME1 nucleic acid or ME1 protein by determining the amount of ME1 nucleic acid or ME1 protein in the biological sample, comparing the amount of ME1 nucleic acid or ME1 protein in the biological sample to a reference value In some embodiments, the amount of ME1 nucleic acid or ME1 protein is measured in a biological sample obtained from the subject.

In some embodiments, the present invention provides a method of detecting synovial sarcoma (SS) in a subject by determining the amount of ME1 nucleic acid or ME1 protein in a biological sample obtained from a subject; and detecting SS in the subject when the amount of ME1 nucleic acid or ME1 protein is absent, zero or near zero.

In some embodiments, the present invention provides a method of determining treatment of a subject with cancer by determining the amount of ME1 nucleic acid or ME1 protein in a biological sample obtained from the subject, and treating the subject with an inducer of ferroptosis when the amount of ME1 nucleic acid or ME1 protein is absent, zero or near zero.

In some embodiments, the present invention provides a method for selecting patients or patient population for a clinical trial including determining the amount of ME1 nucleic acid or ME1 protein in a biological sample obtained from the prospective patient; comparing the amount of ME1 nucleic acid or ME1 protein to one or more reference values that are indicative of a disease or condition that is to be treated in the clinical trial; and determining the likelihood that a patient is a good candidate for the clinical trial based on the presence, absence or level of ME1 nucleic acid or ME1 protein that is correlated with success in a clinical trial.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A, FIG. 1B) The synovial sarcoma (SS) cell lines SYO-1 and FUJI, both of which harbor the SYT:SSX2 fusion, demonstrated a unique sensitivity to glucose withdrawal, but not glutamine withdrawal. (FIG. 1C) SS cell lines acutely die as early as two hours as seen by PI FACS. (FIG. 1D) SS cell lines were treated with 2-deoxy-D-glucose, the pharmacological mimic of glucose deprivation, and a similar death phenotype at 48 hours was observed in SYO and FUJI but not the control cell lines SKLMS-1 and MG-63, a uterine leiomyosarcoma (LMS) and osteosarcoma cell line, respectively.

(FIG. 3A and FIG. 3B) Pretreatment with either ZVAD or necrostatin one hour prior to glucose-free media change did not result in protection from cell death under glucose deprivation conditions. (FIG. 3C and FIG. 3D) Pretreatment with ferrostatin, a small-molecule inhibitor of ferroptosis, produced significant protection from glucose-deprivation mediated cell death under similar conditions. (FIG. 3E and FIG. 3F) SYO-1 and FUJI cell lines pretreated with deferiprone, a well-established iron chelator, one hour prior to glucose deprivation, displayed significant protection from cell death over an acute time course of 2-6 hours.

FIG. 5A, FIG. 5B, FIG. 5C, FIG. 5D, FIG. 5E, FIG. 5F, and FIG. 5G depict graphs showing that SYO-1 and FUJI experience rapid oxidative cell death under glucose deprivation conditions. (FIG. 5A and FIG. 5B) Protection from cell death was noted at 2 and 6 hours when SYO-1 and FUJI were pretreated with 10 mM NAC, an antioxidant, one hour prior to glucose deprivation. (FIG. 5D and FIG. 5E) Examination of the production of ROS via hydrogen peroxide ($H_2O_2$) accumulation under glucose deprivation conditions of just 15 minutes in SYO-1 and FUJI revealed a rapid accumulation of $H_2O_2$ in the glucose-free wells when compared to the non-treatment wells. (FIG. 5D-FIG. 5G) FACS analysis of ROS generation in both SS lines, SKLMS-1 and MG-63 at baseline, 15 minutes and 30 minutes of glucose deprivation revealed a rapid increase of total ROS levels at 15 minutes and 30 minutes in SYO-1 and FUJI (FIG. 5D and FIG. 5E) when compared with SKLMS-1 and MG-63 (FIG. 5F and FIG. 5G).

(FIG. 8A) Both upper glycolysis and the PPP were reliably depleted without a source of glucose, validating the true glucose deprivation condition under which SS was studied. The bars/lines represent absolute concentrations of each metabolite in SYO-1 control (blue), SYO-1 (−) glucose (red), FUJI control (green), FUJI (−) glucose (orange), respectively. (FIG. 8B, FIG. 8C, and FIG. 8D) Examination of the redox balance of SYO-1 and FUJI under normal and glucose deprivation conditions revealed a decrease in glutathione (GSH) and statistically significant increase in glutathione disulfide (GSSG), the reduced form of GSH, as well as a statistically significant difference in the ratio of GSH to GSSG. (FIG. 8E, FIG. 8F, and FIG. 8G) Under glucose deprivation conditions, NADPH levels are statistically significantly decreased, as is the ratio of NADPH to NADP+.

(FIG. 9A) The expression of ME1 was noted to be absent in both SYO-1 and FUJI when compared to a panel of additional cell lines. (FIG. 9B) RNA microarray analysis confirmed a dramatic loss of ME1 expression in 40 SS clinical samples when compared to over 100 leiomyosarcoma (LMS), dedifferentiated liposarcoma, pleiomorphic and undifferentiated sarcomas, normal abdominal adipose tissue, and normal skeletal muscle tissue samples. (FIG. 9C) mRNA expression of ME1 in SS is significantly lower than that of dedifferentiated liposarcoma, leiomyosarcoma, myxosarcoma, and undifferentiated pleiomorphic sarcoma per TCGA analysis. (FIG. 9D) Investigation into ME1 expression of the SYT-SSX1 and SYT-SSX2 transgenic mouse models revealed a significant decrease in ME1 expression in tumor tissue when compared with the control tissue, mouse muscle. (FIG. 9E) Examination of tumor lysates from 14 different SYT-SSX transgenic mouse models (7 from SSX1, 7 from SSX2) revealed a similar lack of ME1 expression when compared to NIH3T3 cells (embryonic mouse kidney/liver).

FIG. 10A, FIG. 10B, FIG. 10C, FIG. 10D, FIG. 10E, FIG. 10F and FIG. 10G depict immunohistochemistry of SS clinical samples analyzed for ME1 expression. SS demonstrated two patterns. The first, purely monophasic in morphology, was noted in 5/20 samples that were completely negative for ME1. The second pattern appeared to be a "starry sky pattern" where occasional sporadic cells are positive but the majority (99%) are negative, and was noted in 8/20 samples. More interestingly, in biphasic SS tumors, while the sarcomatous portion of the tumor lacks ME1 expression, the biphaisic carcinomatous portion of the tumor is positive for ME1.

(FIG. 11A) In MG63, an osteosarcoma, and A549, a lung carcinoma, all constructs displayed marked ME1 knockdown. (FIG. 11B) With effective knockdown of ME1, marked sensitivity to glucose deprivation over an acute time period was conferred to these cell lines with inherent ME1 expression. (FIG. 11C) Although introduction of the ME1 construct into SS cell lines via infection was uniformly lethal, overexpression of ME1 via transfection was observed.

FIG. 12A, FIG. 12B, FIG. 12C, FIG. 12D, FIG. 12E, FIG. 12F, FIG. 12G and FIG. 12H depict graphs showing that inhibition of G6PD leads to cell death and sigma2-erastin inhibits tumor growth in vivo. (FIG. 12A, FIG. 12B) Treatment with dehydroepiandrosterone (DHEA), a G6PD inhibitor, over a course of 48 hours, resulted in varied but significant cell death in both SYO-1 and FUJI. PDD2958 displayed a 2 log improvement in the IC50 when compared with DHEA itself. (FIG. 12C, FIG. 12D, and FIG. 12E) Treatment of SYO-1 and FUJI cell lines with erastin compounds resulted in significant cell death at 24 hours when compared with SKLMS-1 and MG-63. (FIG. 12F) When SYO-1 was grafted into a murine model, a dramatic decrease in tumor size was observed with a dose of 1 mg/day of DHEA for 12 days, a dose and regimen that was well-tolerated by the murine model, and persisted after cessation of treatment. (FIG. 12G, FIG. 12H) In the in vivo murine model, treatment with sigma erastin resulted in a significant slow in tumor growth when compared to the control vehicle, sigma ligand, sigma ligand and erastin, and erastin arms of the experiment.

(FIG. 13A) ChIP of the ME1 promoter revealed that the SYT-SSX translocation indirectly suppresses ME1. (FIG. 13B) MS-PCR was performed. Genomic DNA was isolated, bisulphite conversion performed, and methylation-specific PCR of a 152 bp fragment located within a CpG island was used to determine the methylation status of the ME1 promotor. Both SYO-1 and FUJI had highly methylated ME1 promoters.

DETAILED DESCRIPTION OF THE INVENTION

Figure 1A:
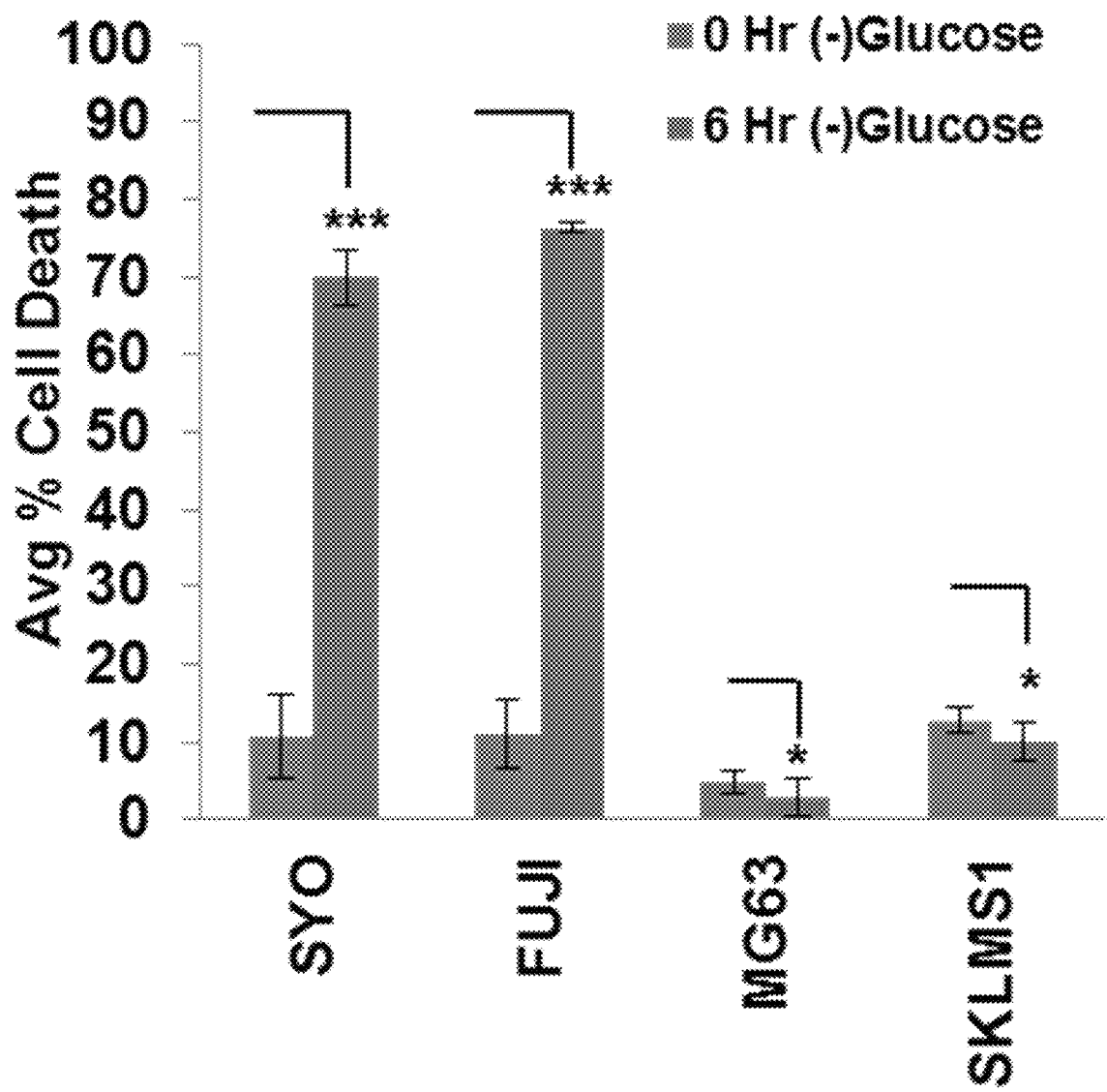
FIG. 1A, FIG. 1B, FIG. 1C and FIG. 1D depict graphs showing that synovial sarcoma cell lines are glucose addicted.

The inventors have discovered that a tumor absent expression of malic enzyme 1 (ME1) specifically responds to treatment with an inducer of ferroptosis. Specifically, the inventors show that synovial sarcoma lacking ME1 expression are sensitive to treatment with a sigma-erastin compound. Various aspects of the methods of the disclosure are discussed in more detail below.

I. Methods

In an aspect, the disclosure provides a method to classify a subject based on the amount of ME1 nucleic acid or ME1 protein measured in a biological sample obtained from the subject. The method generally comprises (a) determining the amount of ME1 nucleic acid or ME1 protein in the biological sample, (b) comparing the amount of ME1 nucleic acid or ME1 protein in the biological sample to a reference value, and (c) classifying the subject as having an increased or decreased amount ME1 nucleic acid or ME1 protein based on the amount ME1 nucleic acid or ME1 protein measured in the sample.

In another aspect, the disclosure provides a method of detecting synovial sarcoma (SS) in a subject. The method comprises: (a) determining the amount of ME1 nucleic acid or ME1 protein in a biological sample obtained from a subject; and (b) detecting SS in the subject when the amount of ME1 nucleic acid or ME1 protein is zero or near zero. Additionally, the method of detecting SS in a subject comprises (a) determining the presence or absence of ME1 nucleic acid or ME1 protein in a biological sample obtained from the subject, and (b) detecting SS in the subject when ME1 nucleic acid or ME1 protein is absent.

In still another aspect, the disclosure provides a method of determining treatment of a subject with cancer. The method generally comprises (a) determining the amount of ME1 nucleic acid or ME1 protein in a biological sample obtained from the subject, and (b) treating the subject with an inducer of ferroptosis when the amount of ME1 nucleic acid or ME1 protein is zero or near zero. Alternatively, the method of determining treatment of a subject with cancer comprises (a) determining the presence or absence of ME1 nucleic acid or ME1 protein in a biological sample obtained from the subject, and (b) treating the subject with an inducer of ferroptosis when ME1 nucleic acid or ME1 protein is absent.

In one embodiment, the invention provides a method for selecting patients or patient population for a clinical trial comprising (a) determining the amount of ME1 nucleic acid or ME1 protein in a biological sample obtained from the prospective patient; (b) comparing the amount of ME1 nucleic acid or ME1 protein to one or more reference values that are indicative of a disease or condition that is to be treated in the clinical trial; and (c) determining the likelihood that a patient is a good candidate for the clinical trial based on the presence, absence or level of ME1 nucleic acid or ME1 protein that is correlated with success in a clinical trial.

In any of the foregoing embodiments, the subject may or may not be diagnosed with cancer. In certain embodiments, the subject may not be diagnosed with cancer but is suspected of having cancer based on symptoms. Symptoms of cancer that may lead to a diagnosis are dependent upon the cancer and are known to those of skill in the art. In other embodiments, the subject may not be diagnosed with cancer but is at risk of having cancer. Risk factors for cancer are dependent upon the cancer and are known to those of skill in the art. In other embodiment, the subject has no symptoms and/or no risk factors for cancer. Methods of diagnosing cancer are dependent upon the cancer and are known to those of skill in the art. For example, the NCCN guidelines provides comprehensive disclosures of detection, prevention and risk reduction (nccn.org).

Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In an embodiment, the animal is a laboratory animal. Non-limiting examples of a laboratory animal may include rodents, canines, felines, and non-human primates. In certain embodiments, the animal is a rodent. In a preferred embodiment, the subject is human.

(a) Biological Sample

As used herein, the term "biological sample" refers to a sample obtained from a subject. Any biological sample containing ME1 protein or ME1 nucleic acid is suitable. Numerous types of biological samples are known in the art. Suitable biological sample may include, but are not limited to, tissue samples or bodily fluids. In some embodiments, the biological sample is a tissue sample such as a tissue biopsy. The biopsied tissue may be fixed, embedded in paraffin or plastic, and sectioned, or the biopsied tissue may be frozen and cryosectioned. In other embodiments, the sample may be a bodily fluid. Non-limiting examples of suitable bodily fluids include blood, plasma, serum, urine, saliva, sputum, ascites, tears, mucus from gastrointestinal tracts, and pleural effusion. The fluid may be used "as is", the cellular components may be isolated from the fluid, or a fraction may be isolated from the fluid using standard techniques.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that the ME1 nucleic acid or ME1 protein can be accurately detected and the amount measured according to the disclosure.

In some embodiments, a single sample is obtained from a subject to detect ME1 nucleic acid or ME1 protein in the sample. Alternatively, ME1 nucleic acid or ME1 protein may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16 or more samples are collected from a subject over time.

When more than one sample is collected from a subject over time, samples may be collected every 1, 2, 3, 4, 5, 6, 7, 8, 9, 10, 11, 12 or more days. In some embodiments, a sample is collected about every 6 days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days. In still other embodiments, samples are collected a month apart, 3 months apart, 6 months apart, 1 year apart, 2 years apart, 5 years apart, 10 years apart or more.

(b) Detecting ME1 Nucleic Acid or ME1 Protein

Once a sample is obtained, it is processed in vitro to detect and measure the amount of ME1 nucleic acid or ME1 protein. All suitable methods for detecting and measuring an amount of ME1 nucleic acid or ME1 protein known to one of skill in the art are contemplated within the scope of the invention. Methods of detecting nucleic acid expression and protein expression are described in detail below.

The amount of ME1 nucleic acid or ME1 protein measured in the biological sample may be used to determine treatment for cancer. More specifically, when ME1 nucleic acid or ME1 protein is zero or near zero or absent, the subject may be treated with an inducer of ferroptosis. As used herein, "zero" or "absent" means that the amount of ME1 nucleic acid or ME1 protein measured is at or near the baseline signal. As used herein, "near zero" means that the amount of ME1 nucleic acid or ME1 protein measured is no more than 10%, no more than 9%, no more than 8%, no more than 7%, no more than 6%, no more than 5%, no more than 4%, no more than 3%, no more than 2%, or no more than 1% above baseline. As used herein, "baseline" is the background of the assay used. For example, baseline may be the background staining of the biological sample. Additionally, baseline may be the background signal from PCR. A skilled artisan would be able to determine the level of background based on the assay by using, for example, a negative control and identify if ME1 nucleic acid or ME1 protein is zero or near zero or absent. The presence of positive and negative controls will facilitate an improved confidence in identifying if ME1 nucleic acid or ME1 protein is zero or near zero or absent.

In one embodiment, the amount of ME1 nucleic acid or ME1 protein protein can be compared using the ratio of the amount of ME1 nucleic acid or ME1 protein in the biological sample as compared with the reference value. For example, a nucleic acid or protein is differentially expressed if the ratio of the amount of ME1 nucleic acid or ME1 protein in the biological sample as compared with the reference value is greater than or less than 1.0. For example, a ratio of greater than 1, 1.2, 1.5, 1.7, 2, 3, 4, 5, 10, 15, 20 or more, or a ratio less than 1, 0.8, 0.6, 0.4, 0.2, 0.1, 0.05, 0.001 or less. In another embodiment, the increase or decrease in amount is measured using p-value. For instance, when using p-value, ME1 nucleic acid or ME1 protein is identified as being differentially expressed between ME1 nucleic acid or ME1 protein in a biological sample and the reference value when the p-value is less than 0.1, preferably less than 0.05, more preferably less than 0.01, even more preferably less than 0.005, the most preferably less than 0.001. In another embodiment, the increase or decrease in amount is measured using fold change. For example, ME1 nucleic acid or ME1 protein may be increased or decreased by at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 65-fold, at least 70-fold, or at least 75-fold, relative to the reference value.

Any suitable reference value known in the art may be used. For example, a suitable reference value may be the amount of ME1 nucleic acid or ME1 protein in a biological sample obtained from a subject or group of subjects of the same species that has no detectable ME1 nucleic acid or ME1 protein. Additionally, a suitable reference value may be the amount of ME1 nucleic acid or ME1 protein in a biological sample from the same subject taken from a non-diseased portion. Further, a suitable reference value may be the amount of ME1 nucleic acid or ME1 protein in a biological sample obtained from a subject or group of subjects of the same species that has ME1 nucleic acid or ME1 protein expression. Using such a reference value, ME1 nucleic acid or ME1 protein may be identified as zero, near zero, or absent when the amount of ME1 nucleic acid or ME1 protein is at least 2-fold less than the reference value. For example, using such a reference value, ME1 nucleic acid or ME1 protein may be identified as zero, near zero, or absent when the amount of ME1 nucleic acid or ME1 protein is at least 2-fold, at least 3-fold, at least 4-fold, at least 5-fold, at least 10-fold, at least 15-fold, at least 20-fold, or at least 25-fold less than the reference value. Further, using such a reference value, ME1 nucleic acid or ME1 protein may be identified as zero, near zero, or absent when the amount of ME1 nucleic acid or ME1 protein is significantly less than the reference value.

In another example, a suitable reference value may be the amount of ME1 nucleic acid or ME1 protein in a biological sample obtained from a subject or group of subjects of the same species that has no detectable ME1 nucleic acid or ME1 protein. Using such a reference value, ME1 nucleic acid or ME1 protein may be identified as zero, near zero, or absent when the amount of ME1 nucleic acid or ME1 protein is less than 2-fold different than the reference value. Further, using such a reference value, ME1 nucleic acid or ME1 protein may be identified as zero, near zero, or absent when the amount of ME1 nucleic acid or ME1 protein is not significantly different from the reference value.

In another example, a suitable reference value may be the amount of ME1 nucleic acid or ME1 protein in a biological sample obtained from a subject or group of subjects of the same species that has synovial sarcoma (SS) as measured via standard methods. Using such a reference value, ME1 nucleic acid or ME1 protein may be identified as zero, near zero, or absent when the amount of ME1 nucleic acid or ME1 protein is less than 2-fold different than the reference value. Further, using such a reference value, ME1 nucleic acid or ME1 protein may be identified as zero, near zero, or absent when the amount of ME1 nucleic acid or ME1 protein is not significantly different than the reference value.

i. Nucleic Acid Expression

In an embodiment, ME1 nucleic acid expression may be measured to determine the amount of ME1 nucleic acid in a biological sample. In a specific embodiment, ME1 mRNA may be measured to determine the amount of ME1 nucleic acid in a biological sample. In another embodiment, ME1 nucleic acid expression may be detected to determine the presence or absence of ME1 nucleic acid in a biological sample. In a specific embodiment, ME1 mRNA may be detected to determine the presence or absence of ME1 nucleic acid in a biological sample.

Methods for detecting and/or assessing an amount of nucleic acid expression in a sample are well known in the art, and all suitable methods for detecting and/or assessing an amount of nucleic acid expression known to one of skill in the art are contemplated within the scope of the invention. The term "amount of nucleic acid expression" or "level of nucleic acid expression" as used herein refers to a measurable level of expression of the nucleic acids, such as, without limitation, the level of messenger RNA (mRNA) transcript expressed or a specific variant or other portion of the mRNA, the enzymatic or other activities of the nucleic acids, and the level of a specific metabolite. The term "nucleic acid" includes DNA and RNA and can be either double stranded or single stranded. Non-limiting examples of suitable methods to assess an amount of nucleic acid expression may include arrays, such as microarrays, PCR, such as RT-PCR (including quantitative RT-PCR), nuclease protection assays and Northern blot analyses. In a specific embodiment, determining the amount of expression of a target nucleic acid comprises, in part, measuring the level of target nucleic acid mRNA expression.

In one embodiment, the amount of nucleic acid expression or the presence or absence of nucleic acid may be determined by using an array, such as a microarray. Methods of using a nucleic acid microarray are well and widely known in the art. For example, a nucleic acid probe that is complementary or hybridizable to an expression product of a target gene may be used in the array. The term "hybridize"

or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In another embodiment, the amount of nucleic acid expression or the presence or absence of nucleic acid may be determined using PCR. Methods of PCR are well and widely known in the art, and may include quantitative PCR, semi-quantitative PCR, multiplex PCR, or any combination thereof. Specifically, the amount of nucleic acid expression or the presence or absence of nucleic acid may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The amount of nucleic acid expression or the presence or absence of nucleic acid may be determined by measuring an entire mRNA transcript for a nucleic acid sequence, or measuring a portion of the mRNA transcript for a nucleic acid sequence. For instance, if a nucleic acid array is utilized to measure the amount of mRNA expression or the presence or absence of mRNA, the array may comprise a probe for a portion of the mRNA of the nucleic acid sequence of interest, or the array may comprise a probe for the full mRNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. This allows comparisons between assays that are performed on different occasions.

ii. Protein Expression

In another embodiment, ME1 protein expression may be measured to determine the amount of ME1 protein in a biological sample. In a specific embodiment, ME1 protein expression may be measured using an ELISA to determine the amount of ME1 protein in a biological sample. In another embodiment, ME1 protein expression may be detected using an immunoassay to determine the presence or absence of ME1 protein in a biological sample. In a specific embodiment, ME1 protein expression may be detected using an ELISA to determine the presence or absence of ME1 protein in a biological sample.

Methods for detecting and/or assessing an amount of protein expression are well known in the art, and all suitable methods for detecting and/or assessing an amount of protein expression known to one of skill in the art are contemplated within the scope of the invention. Non-limiting examples of suitable methods to detect and/or assess an amount of protein expression may include epitope binding agent-based methods and mass spectrometry based methods.

In some embodiments, the method to detect and/or assess an amount of protein expression is mass spectrometry. By exploiting the intrinsic properties of mass and charge, mass spectrometry (MS) can resolve and confidently identify a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can use mass spectrometry to look for the level of protein encoded from a target nucleic acid of the disclosure.

In some embodiments, the method to detect and/or assess an amount of protein expression is an epitope binding agent-based method. As used herein, the term "epitope binding agent" refers to an antibody, an aptamer, a nucleic acid, an oligonucleic acid, an amino acid, a peptide, a polypeptide, a protein, a lipid, a metabolite, a small molecule, or a fragment thereof that recognizes and is capable of binding to a target gene protein. Nucleic acids may include RNA, DNA, and naturally occurring or synthetically created derivative.

As used herein, the term "antibody" generally means a polypeptide or protein that recognizes and can bind to an epitope of an antigen. An antibody, as used herein, may be a complete antibody as understood in the art, i.e., consisting of two heavy chains and two light chains, or may be any antibody-like molecule that has an antigen binding region, and includes, but is not limited to, antibody fragments such as Fab', Fab, F(ab')2, single domain antibodies, Fv, and single chain Fv. The term antibody also refers to a polyclonal antibody, a monoclonal antibody, a chimeric antibody and a humanized antibody. The techniques for preparing and using various antibody-based constructs and fragments are well known in the art. Means for preparing and characterizing antibodies are also well known in the art (See, e.g. Antibodies: A Laboratory Manual, Cold Spring Harbor Laboratory, 1988; herein incorporated by reference in its entirety).

As used herein, the term "aptamer" refers to a polynucleotide, generally a RNA or DNA that has a useful biological activity in terms of biochemical activity, molecular recognition or binding attributes. Usually, an aptamer has a molecular activity such as binging to a target molecule at a specific epitope (region). It is generally accepted that an aptamer, which is specific in it binding to a polypeptide, may be synthesized and/or identified by in vitro evolution methods. Means for preparing and characterizing aptamers, including by in vitro evolution methods, are well known in the art (See, e.g. U.S. Pat. No. 7,939,313; herein incorporated by reference in its entirety).

In general, an epitope binding agent-based method of detecting and/or assessing an amount of protein expression comprises contacting a sample comprising a polypeptide with an epitope binding agent specific for the polypeptide under conditions effective to allow for formation of a complex between the epitope binding agent and the polypeptide. Epitope binding agent-based methods may occur in solution, or the epitope binding agent or sample may be immobilized on a solid surface. Non-limiting examples of suitable surfaces include microtitre plates, test tubes, beads, resins, and other polymers.

An epitope binding agent may be attached to the substrate in a wide variety of ways, as will be appreciated by those in the art. The epitope binding agent may either be synthesized first, with subsequent attachment to the substrate, or may be directly synthesized on the substrate. The substrate and the epitope binding agent may be derivatized with chemical functional groups for subsequent attachment of the two. For example, the substrate may be derivatized with a chemical functional group including, but not limited to, amino groups, carboxyl groups, oxo groups or thiol groups. Using these functional groups, the epitope binding agent may be attached directly using the functional groups or indirectly using linkers.

The epitope binding agent may also be attached to the substrate non-covalently. For example, a biotinylated epitope binding agent may be prepared, which may bind to surfaces covalently coated with streptavidin, resulting in attachment. Alternatively, an epitope binding agent may be synthesized on the surface using techniques such as photopolymerization and photolithography. Additional methods of attaching epitope binding agents to solid surfaces and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, both of which are hereby incorporated by reference in their entirety).

Contacting the sample with an epitope binding agent under effective conditions for a period of time sufficient to allow formation of a complex generally involves adding the epitope binding agent composition to the sample and incubating the mixture for a period of time long enough for the epitope binding agent to bind to any antigen present. After this time, the complex will be washed and the complex may be detected by any method well known in the art. Methods of detecting the epitope binding agent-polypeptide complex are generally based on the detection of a label or marker. The term "label", as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, Ni2+, Flag tags, myc tags, heavy metals, and enzymes (including alkaline phosphatase, peroxidase, and luciferase). Methods of detecting an epitope binding agent-polypeptide complex based on the detection of a label or marker are well known in the art.

In some embodiments, an epitope binding agent-based method is an immunoassay. Immunoassays can be run in a number of different formats. Generally speaking, immunoassays can be divided into two categories: competitive immunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In an embodiment, the epitope binding agent method is an immunoassay. In another embodiment, the epitope binding agent method is selected from the group consisting of an enzyme linked immunoassay (ELISA), a fluorescence based assay, a dissociation enhanced lanthanide fluoroimmunoassay (DELFIA), a radiometric assay, a multiplex immunoassay, and a cytometric bead assay (CBA). In some embodiments, the epitope binding agent-based method is an enzyme linked immunoassay (ELISA). In other embodiments, the epitope binding agent-based method is a radioimmunoassay. In still other embodiments, the epitope binding agent-based method is an immunoblot or Western blot. In alternative embodiments, the epitope binding agent-based method is an array. In another embodiment, the epitope binding agent-based method is flow cytometry. In different embodiments, the epitope binding agent-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

(c) Treating or Selecting Patients for a Clinical Trial

The amount of ME1 nucleic acid or ME1 protein measured in the biological sample may be used to determine treatment for cancer or for the selection of patients which would provide a successful population for a clinical trial. More specifically, when ME1 nucleic acid or ME1 protein is zero or near zero or absent, the subject may be treated with an inducer of ferroptosis or selected as a patient of a clinical trial testing the same. Ferroptosis is a type of programmed cell death dependent on iron and characterized by energetic, non-apoptotic, oxidative cell death. As used herein, "an inducer of ferrotoposis" is any molecule that activates cell death via ferroptosis. Accordingly, an inducer of ferroptosis is a molecule that mediates cell death by an iron-dependent, non-apoptotic, oxidative process. One of the skill in the art would be able to identify molecules that induce ferroptosis. For example, a molecule of interest that induces ferroptosis kills cells in a non-apoptotic matter such that inhibition of apoptosis, necrosis, necroptosis, and autophagy by small molecule inhibitors cannot reverse the cell death induced by the molecule of interest. In contrast, antioxidants (e.g., vitamin E) and iron chelators (i.e. deferoxamine mesylate) block cell death induced by the molecule of interest. See, Xie et al., *Cell Death and Differentiation* 2016; 23: 369-379, the disclosure of which is hereby incorporated by reference in its entirety, for method to identify inducers of ferroptosis and examples of inducers of ferroptosis. Non-limiting examples of inducer of ferroptosis include erastin, RSL3, RSL5, FIN, DPI7, buthionine sulfoximine, acetaminophen, sulfasalazine, sorafenib, artesunate, lanperisone, piperazine erastin, and 1S,3R-RSL3. Specifically, an inducer of ferroptosis may be an erastin or an analogue thereof. To improve tumor uptake, an erastin or analogue thereof may be conjugated to a tumor targeting agent. For example, an erastin or analogue thereof may be conjugated to a sigma-2 ligand. More specifically, an inducer of ferroptosis may be a sigma-erastin compound. For example, a sigma-erastin compound may be a compound as detailed in WO 2015153814, the disclosure of which is hereby incorporated by reference in its entirety. In a specific embodiment, the sigma-erastin compound is SWV-49.

The subject or patient may be treated with an inducer of ferroptosis in combination with methods standard in the art for treating cancer. Such treatment methods may depend on the type and severity of the cancer, as well as the general condition of the patient. Treatment of cancer consists primarily of radiation, surgery, chemotherapy and/or targeted therapy. Standard treatment algorithms for each cancer may be found via the National Comprehensive Cancer Network (NCCN) guidelines (nccn.org/professionals/physician_gls/f_guidelines.asp).

The disclosure provides a method of determining treatment of a subject with cancer or selecting a patient population for a clinical trial. As such, the methods of the disclosure may be used to treat a tumor derived from a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, choriocarcinoma, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, glioblastoma, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In certain embodiments, a cancer is selected from the group consisting of synovial sarcoma, Burkitt lymphoma, Hodgkin lymphoma, multiple myeloma, neuroblastoma, glioblastoma, small cell lung cancer, pancreatic cancer, hepatocellular (liver) cancer, endometrial cancer, ovarian cancer, cervical cancer, breast cancer, prostate cancer, bladder cancer, melanoma, rhabdomyosarcoma, osteosarcoma/malignant fibrous histiocytoma of bone, choriocarcinoma, kidney cancer (renal cell cancer), thyroid cancer, and leukemias (acute lymphoblastic, acute myeloid, chronic lymphocytic, and chronic myelogenous). In a specific embodiment, a cancer is synovial sarcoma.

In certain aspects, a pharmacologically effective amount of an inducer of ferroptosis of the disclosure may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the compounds useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

For therapeutic applications, a therapeutically effective amount of an inducer of ferroptosis of the disclosure is administered to a subject. A "therapeutically effective amount" is an amount of the therapeutic composition sufficient to produce a measurable biological response (e.g., a cytotoxic response, or tumor regression). Actual dosage levels of active ingredients in a therapeutic composition of the disclosure can be varied so as to administer an amount of the inducer of ferroptosis that is effective to achieve the desired therapeutic response for a particular subject. The selected dosage level will depend upon a variety of factors including the activity of the therapeutic composition, formulation, the route of administration, combination with other drugs or treatments, cancer size and longevity, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of peptide constructs, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

In certain aspects, the method of the disclosure may further comprise detection of additional genes or proteins for the detection or diagnosis of cancers.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to Examples 1-7

Synovial sarcoma (SS) is a rare and aggressive form of soft tissue sarcoma (STS) with a high metastatic potential. The incidence of SS is estimated at 900-1000 cases per year and accounts for 8-10% of all STS diagnoses in the United States, and is typically diagnosed in young people between the ages of fifteen and forty (Ferrari et al Cancer 2004). Although SS can develop at any anatomic site, it frequently develops as a soft tissue mass in the extremity in approximately 80% of cases. Despite its name, SS rarely involve the actual joint and are not associated with synovial tissue (Eilber et al J Surg Onc 2008). It has been difficult to draw clear conclusions regarding the prognostic factors, treatment outcomes, and survival statistics of SS in adults given the general rarity of the disease. Although SS is viewed as moderately sensitive to cytotoxic chemotherapy, once metastatic, it can result in late recurrence that leads to a poor long-term overall survival. Currently, the 5-year distant recurrence rate, 5-year survival rate, and 10-year survival rate is 39%, 60%, and 34% respectively (Ferrari et al). To date, there is not a targeted therapeutic approach for the treatment of primary or metastatic SS.

Though SS in not associated with a known etiologic agent or genetic predisposition, it has been associated with a gene fusion product between transcription factors SYT on chromosome 18 and one of three homologous genes (SSX1, SSX2, or SSX4) on the X chromosome. This translocation t(x;18) has been identified in 90-95% of all cases of SS, and is pathognomonic and diagnostic for the disease (Sandberg et al. Cancer Genet Cytogenet 2002). Most cases of SYT-SSX translocation-associated SS harbor a fusion between SYT and SSX1 or SSX2, up to 10% of cases carry both translocations, and only rare cases have been shown to carry the SYT-SSX4 translocation (Yang et al Oncogene 2002). The N-terminal domain of SYT, referred to as the SNH domain, is believed to interact with SWI/SNF to alter chromatin remodeling and gene expression, while the C-terminal domain, the QPGY domain, may function as a transcriptional activation domain (Ladanyi M Oncogene 2001). The C-terminal domain of SSX has been established as a dominant repressor domain (SSX-RD) and believed to repress transcription through modification of higher-order chromatin structure (dos Santos H R et al Genes Chromosomes Cancer 2001). Together, the SYT-SSX fusion protein displays both transcriptional activating and repressing domains, has thus resulted in complicated hypotheses regarding its oncogenicity.

As no targeted therapy has been developed for SS, the inventors have applied a metabolic approach to understand the disease. The inventors have identified an acute glucose addiction that is unique to SS and is dependent upon maintenance of the reactive oxygen species balance within the cell. Metabolomic mass spectroscopy has revealed that in acute glucose deprivation, there is a depletion of NADPH and GSH in SS, resulting in a dependence upon the pentose phosphate pathway (PPP) for production of NADPH. The inventors have determined that the PPP dependence is the result of the total lack of expression of malic enzyme 1 (ME1) in SS, which is absent in SS cell lines SYO-1 and FUJI, SS transgenic mouse tumors, and clinical samples by microarray analyses. Malic enzyme 1 is a cytosolic NADP+-dependent protein which serves as a link between glycolysis and the TCA cycle. It catalyzes the oxidative decarboxylation of malate to generate pyruvate and NADPH. It is one of three isoforms in mammalian cells, the other two being malic enzyme 2 (ME2) a mitochondrial NAD(P+) dependent isoform and malic enzyme 3 (ME3) a mitochondrial NADP+-dependent isoform. By recycling malate, the malic enzymes appear to have a regulatory role in matching TCA flux to metabolic demand for biosynthetic precursors. The inventors' findings illustrating both a unique glucose sensitivity, in which SS cells rapidly undergo ferroptosis, as well as lack of expression of ME1 in SS, have allowed them to selectively target this disease via two distinct therapies which have significant potential for tumor control in those patients diagnosed with this rare disease.

Example 1. SS Cell Lines are Glucose Addicted

Figure 1B:
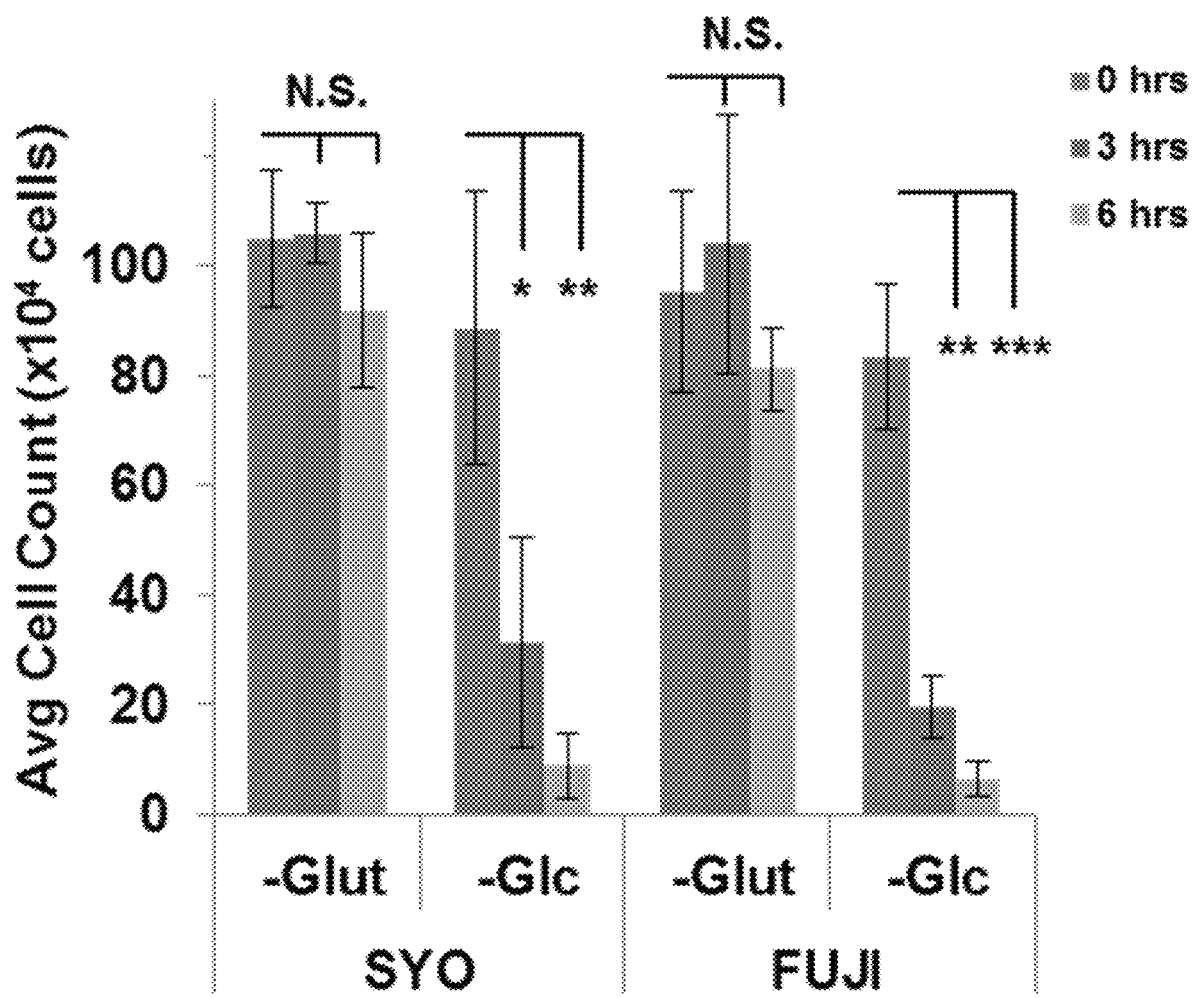
Figure 1C:
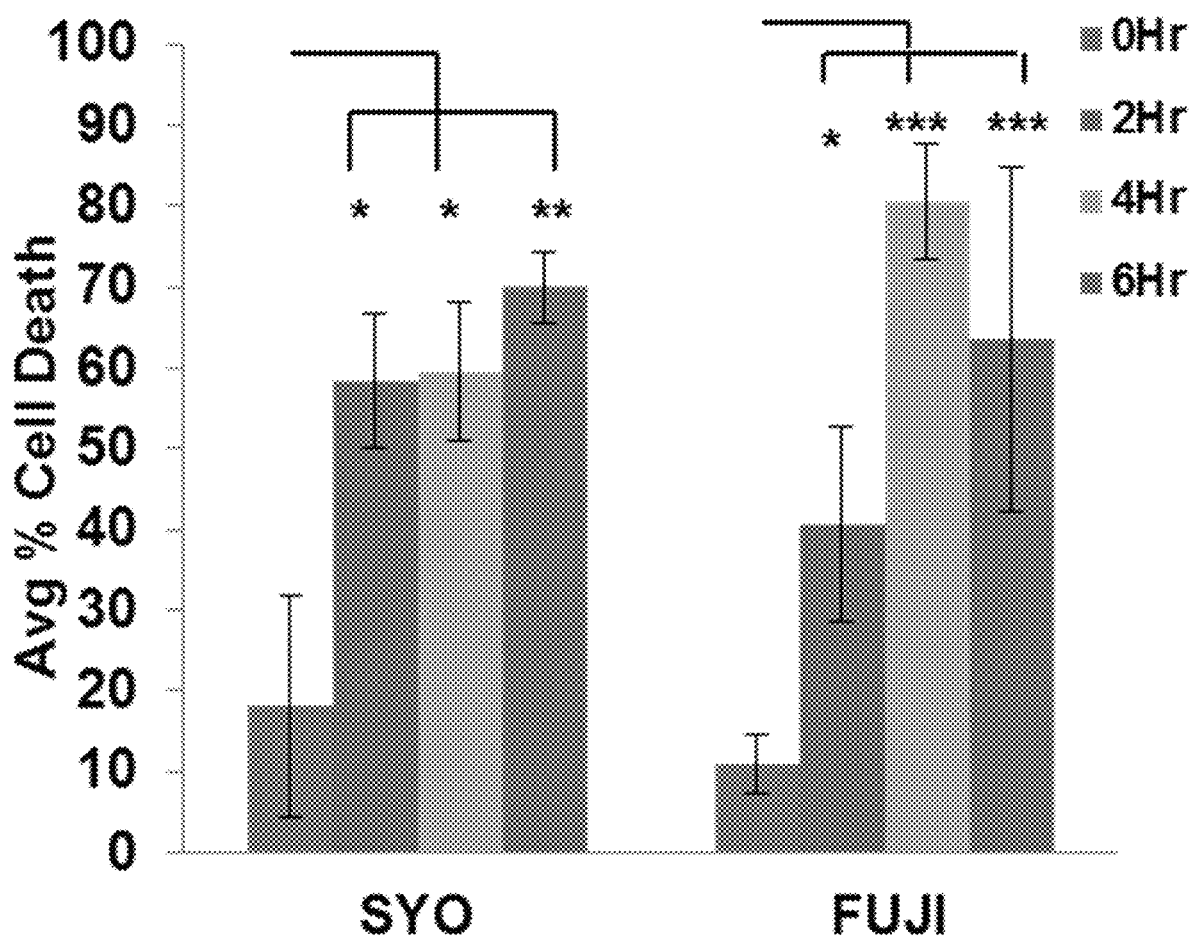
Figure 2:
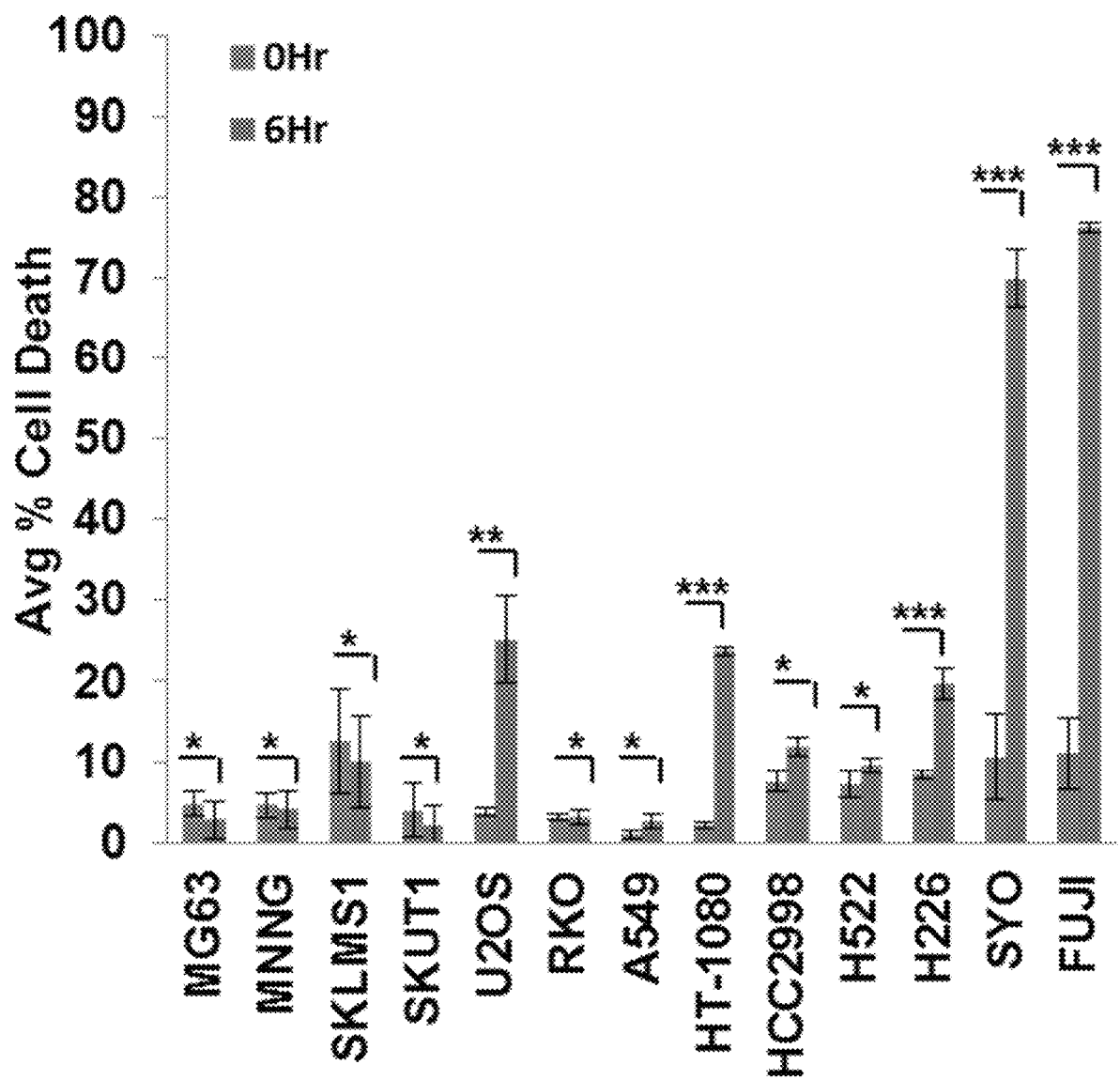
FIG. 2 depicts a graph showing that eleven other non-translocation dependent sarcoma and carcinoma cell lines subjected to glucose withdrawal and PI FACS analysis for 6 hours.

In an effort to identify unique metabolic properties of the subtypes of sarcoma, thirteen sarcoma and carcinoma cell lines were subjected to glucose withdrawal experiments using propidium iodide (PI) FACS to monitor with cell death (FIG. 1A, FIG. 2). Amongst the cell lines tested, the synovial sarcoma (SS) cell lines SYO-1 and FUJI, both of which harbor the SYT:SSX2 fusion, demonstrated a unique sensitivity to glucose withdrawal, but not glutamine withdrawal (FIG. 1B). Starting at thirty minutes to one hour, a rapid loss of cell adherence was seen by trypan blue exclusion as compared to the control cell lines SKLMS1 and MG63 (FIG. 1A). Unlike a majority of cell lines, which can survive and demonstrate no phenotype at 24 hours of glucose withdrawal, SS cell lines acutely die as early as two hours as seen by PI FACS (FIG. 1C). Eleven other non-translocation dependent sarcoma and carcinoma cell lines were then subjected to glucose withdrawal and PI FACS analysis for 6 hours (FIG. 2A) and it was found that the rapid near total acute death after glucose withdrawal to be a unique property of the SS cell lines.

Figure 1D:
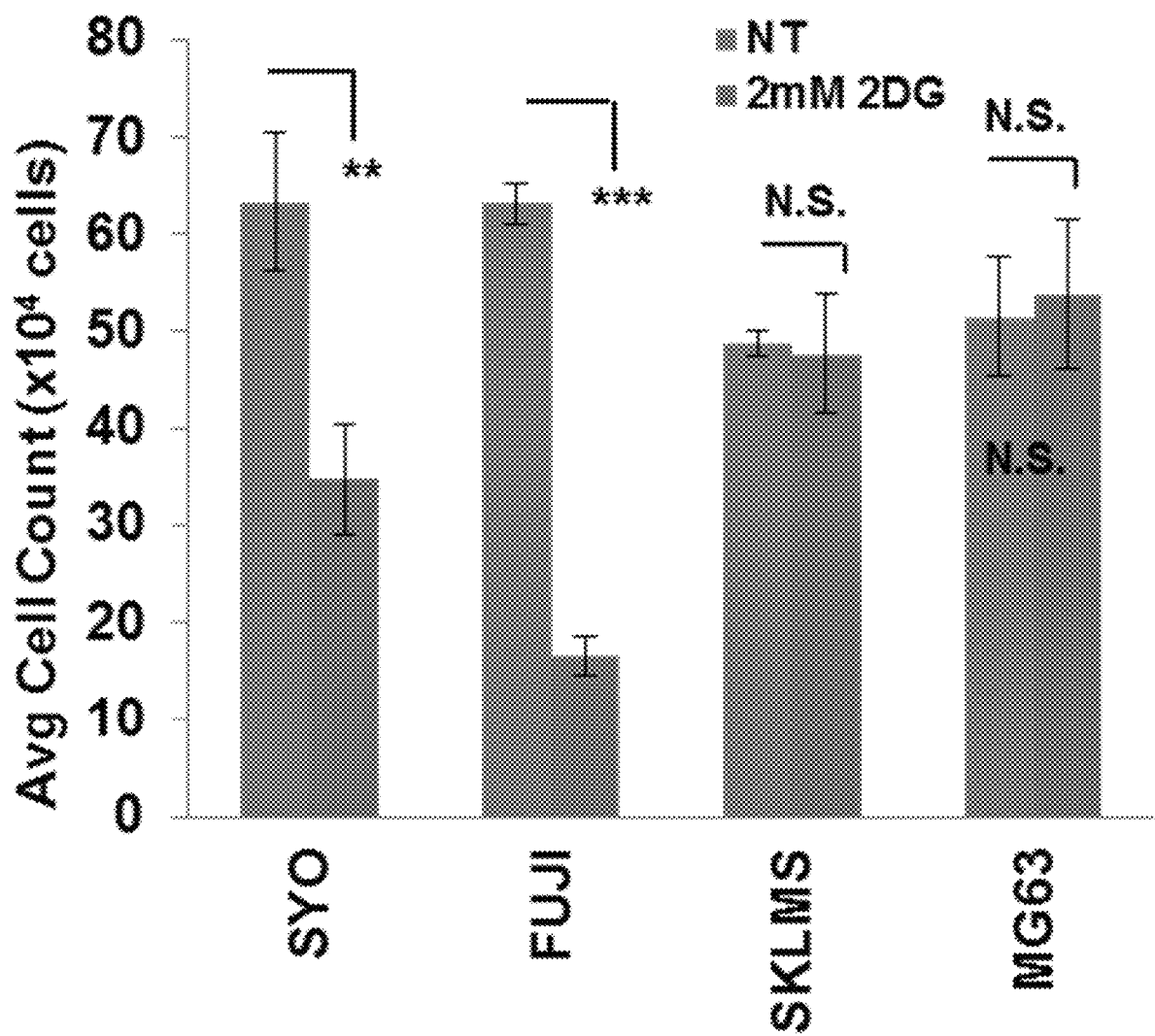

As the rapid cell death suggested a unique glucose addiction, SS cell lines were treated with 2-deoxy-D-glucose, the pharmacological mimic of glucose deprivation, and a similar death phenotype was found at 48 hours in SYO and FUJI but not the control cell lines control cell lines SKLMS-1 and MG-63, a uterine leiomyosarcoma (LMS) and osteosarcoma cell line, respectively (FIG. 1D).

Example 2. Glucose Withdrawal Leads to an Energic Death by Ferroptosis

Figures 3A, 3B:
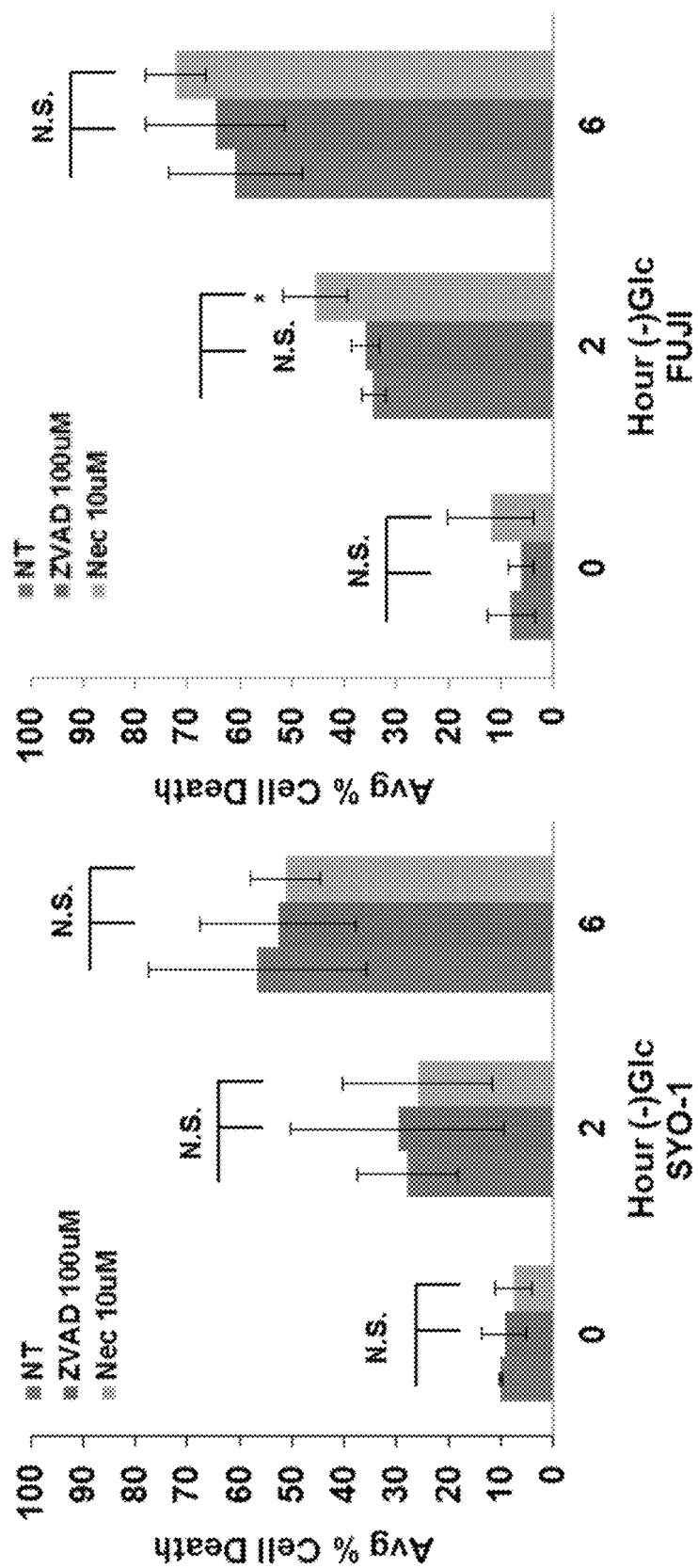
FIG. 3A, FIG. 3B, FIG. 3C, FIG. 3D, FIG. 3E and FIG. 3F depict graphs showing that glucose withdrawal leads to an energetic death by ferroptosis.
Figure 4:
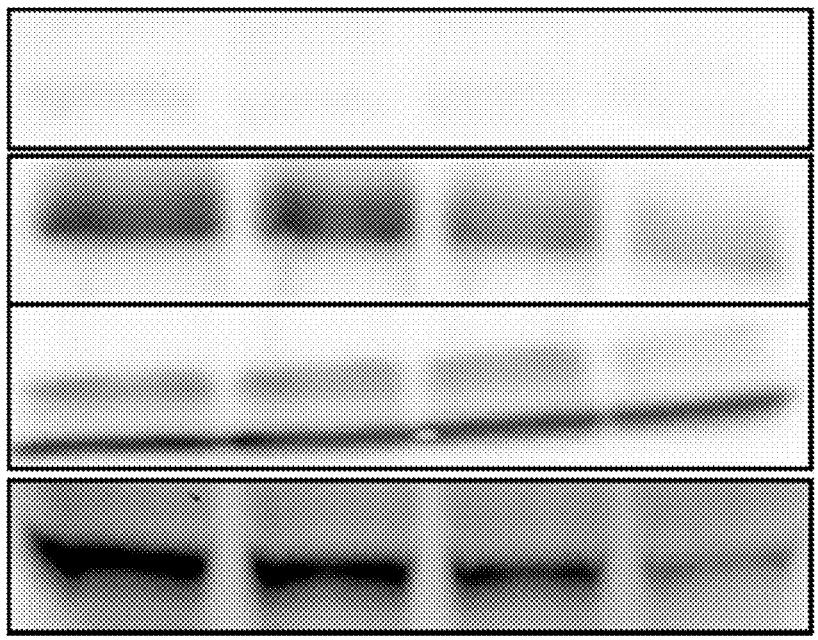
FIG. 4 depicts an immunoblot showing the absence of cleaved parp and cleaved caspase 3 protein under progressive glucose deprivation (0.5, 1, and 2 hours).

To determine the mechanism of cell death under glucose deprivation conditions, cells were pretreated with the inhibitor of apoptosis ZVAD and the inhibitor of necroptosis necrostatin. Pretreatment with either ZVAD or necrostatin one hour prior to glucose-free media change did not result in protection from cell death under glucose deprivation conditions (FIG. 3A and FIG. 3B). Additionally, the absence of cleaved parp and cleaved caspase 3 protein under progressive glucose deprivation (0.5, 1, and 2 hours) further confirmed that apoptosis was not the mechanism of cell death (FIG. 4).

Figure 5C:
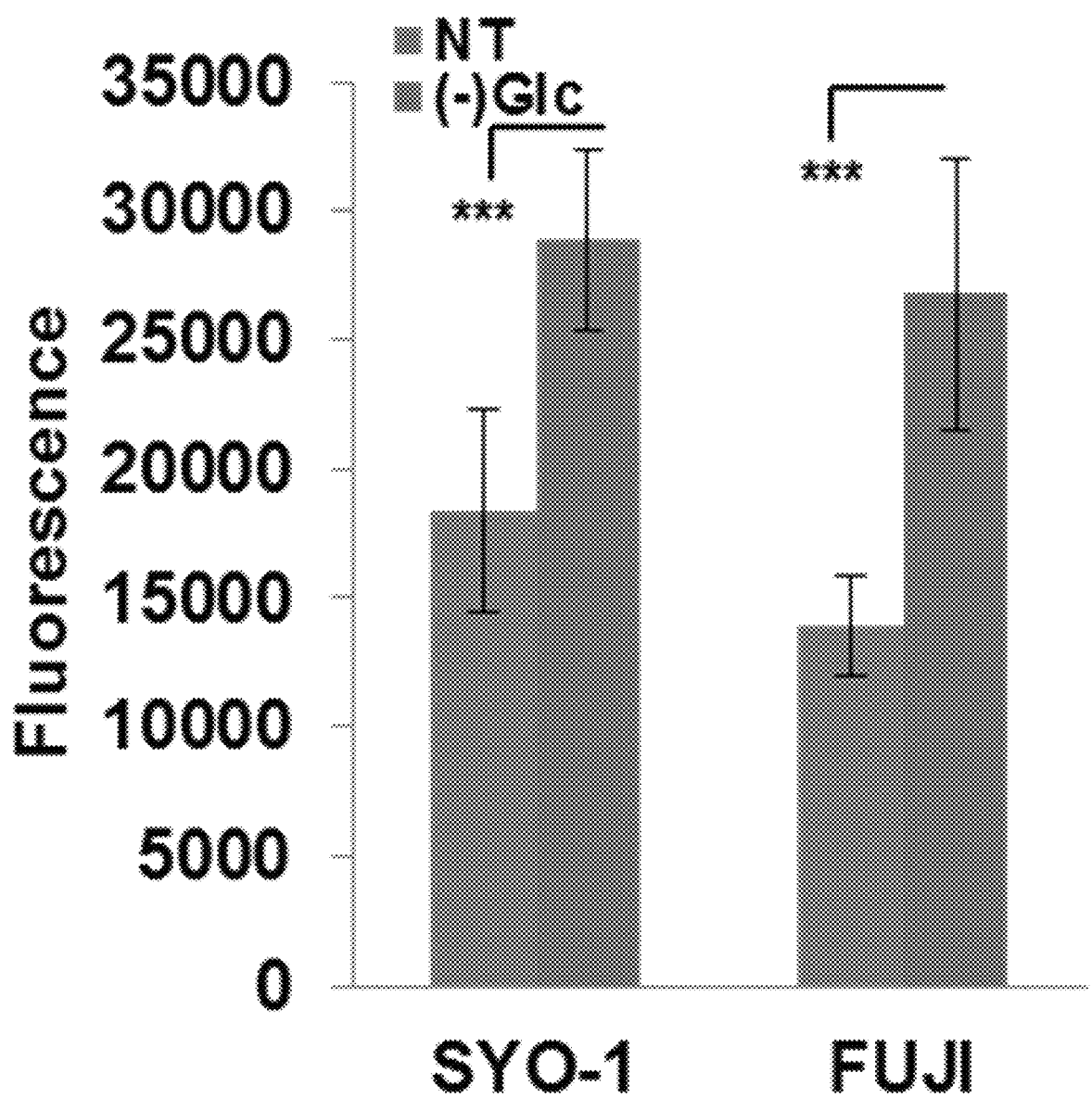
Figures 5F, 5G:
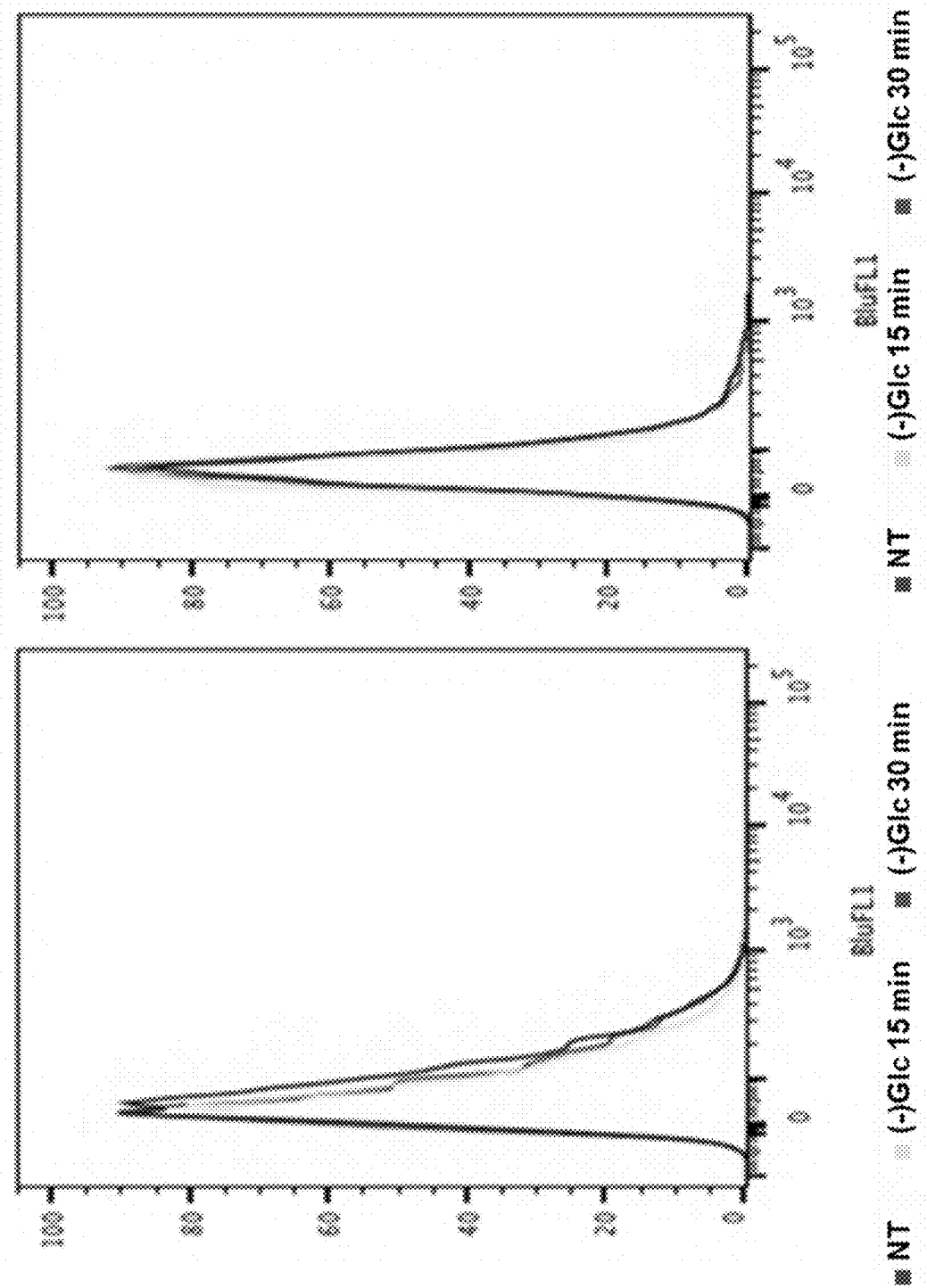

Given the rapidness of SS cell death under glucose deprivation conditions, this suggested an energetic form of cell death. Therefore, the role of ROS in SYO-1 and FUJI cell lines after glucose withdrawal was examined. When SYO-1 and FUJI were pretreated with 10 mM NAC, an antioxidant, one hour prior to glucose deprivation, with the replacement of NAC at the time of glucose-free media change, protection from cell death was noted at 2 and 6 hours (FIG. 5A and FIG. 5B). The production of ROS via hydrogen peroxide ($H_2O_2$) accumulation under glucose deprivation conditions of just 15 minutes in SYO-1 and FUJI was then examined, which revealed a rapid accumulation of $H_2O_2$ in the glucose-free wells when compared to the non-treatment wells (FIG. 5C). Additional FACS analysis of ROS generation in both SS lines, SKLMS-1 and MG-63 at baseline, 15 minutes and 30 minutes of glucose deprivation display a rapid increase of total ROS levels at 15 minutes and 30 minutes in SYO-1 and FUJI when compared with SKLMS-1 and MG-63 (FIG. 5C). Taken together, this evidence of rapid accumulation of ROS under glucose deprivation conditions confirmed that SYO-1 and FUJI experience rapid oxidative cell death under glucose deprivation conditions.

Figures 3C, 3D:
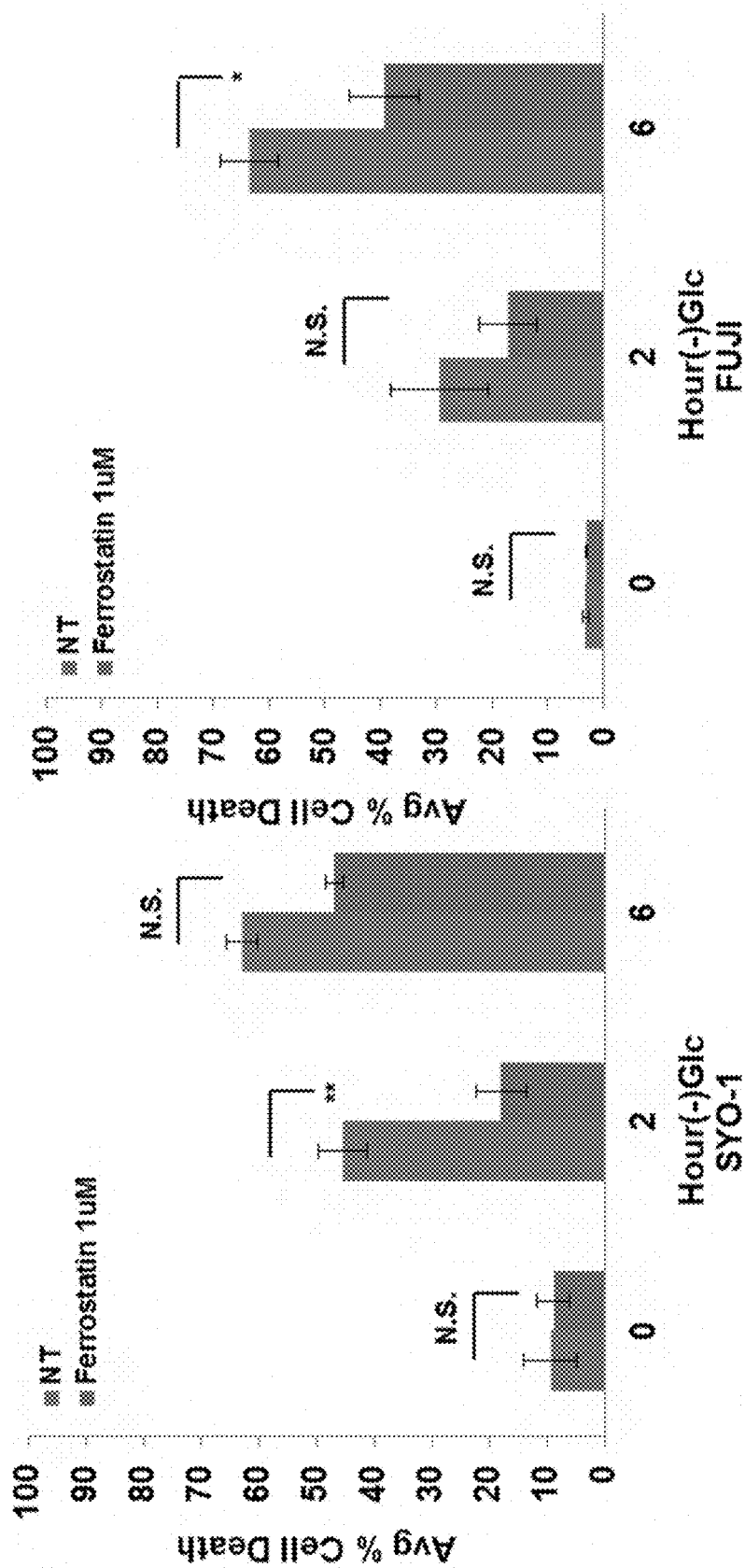
Figures 3E, 3F:
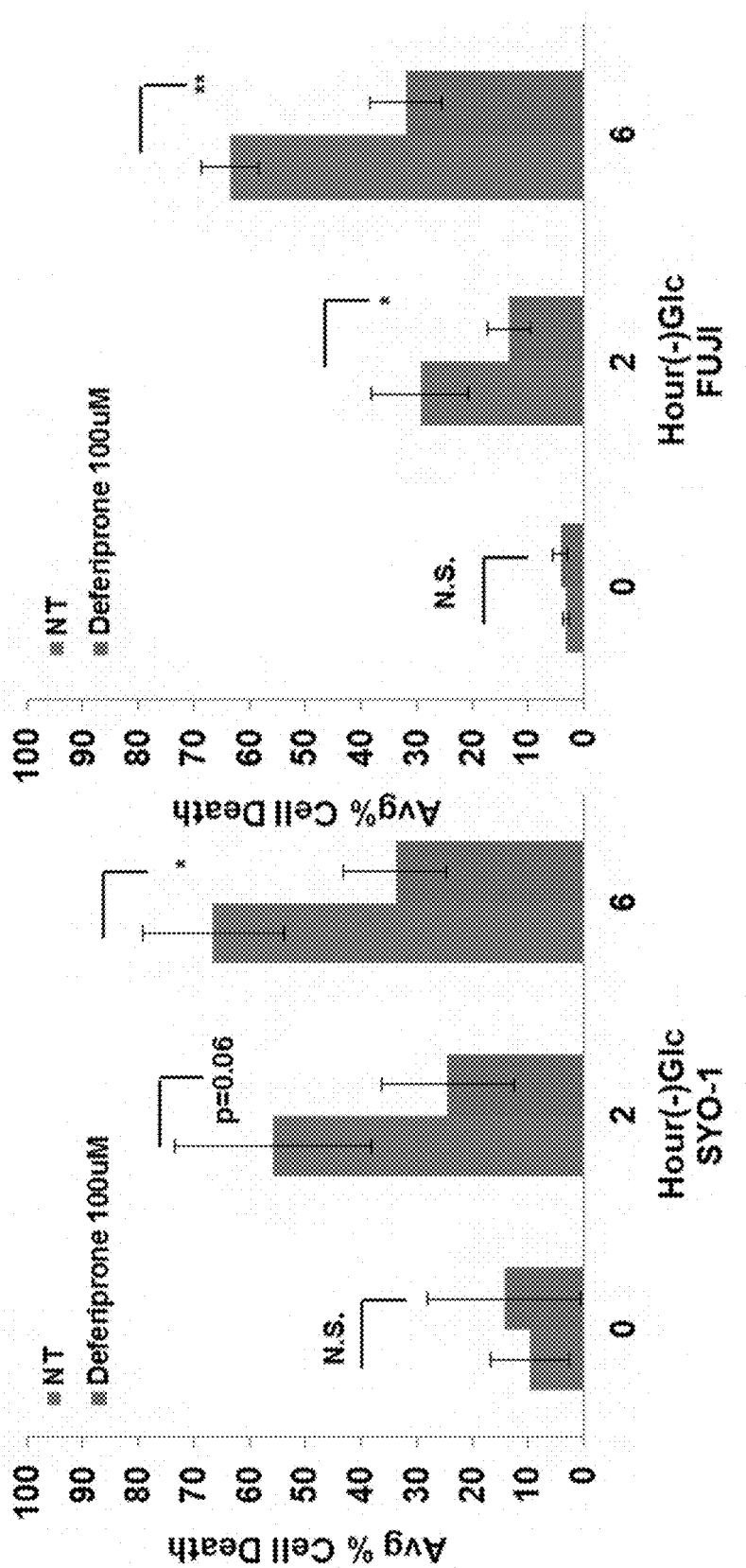

Investigation into additional mechanisms of cell death revealed that an oxidative, energetic form of cell death occurred. Ferroptosis has been hypothesized to involve iron-dependent metabolic dysfunction that results in the production of both cytosolic and lipid ROS. Pretreatment with ferrostatin, a small-molecule inhibitor of ferroptosis, produced significant protection from glucose-deprivation mediated cell death under similar conditions (FIG. 3C and FIG. 3D). Additionally, when SYO-1 and FUJI cell lines were pretreated with deferiprone, a well-established iron chelator, one hour prior to glucose deprivation, there was significant protection from cell death over an acute time course of 2-6 hours (FIG. 3E and FIG. 3F).

Additionally, treatment with erastin, an inducer of ferroptosis, resulted in significant cell death of approximately 40% in as little as 8 hours, suggesting an inherent susceptibility of the SYO-1 and FUJI cell line towards being primed to undergo ferroptosis (FIG. 5C), when compared to control lines SKLMS-1 and MG63.

Figure 7A:
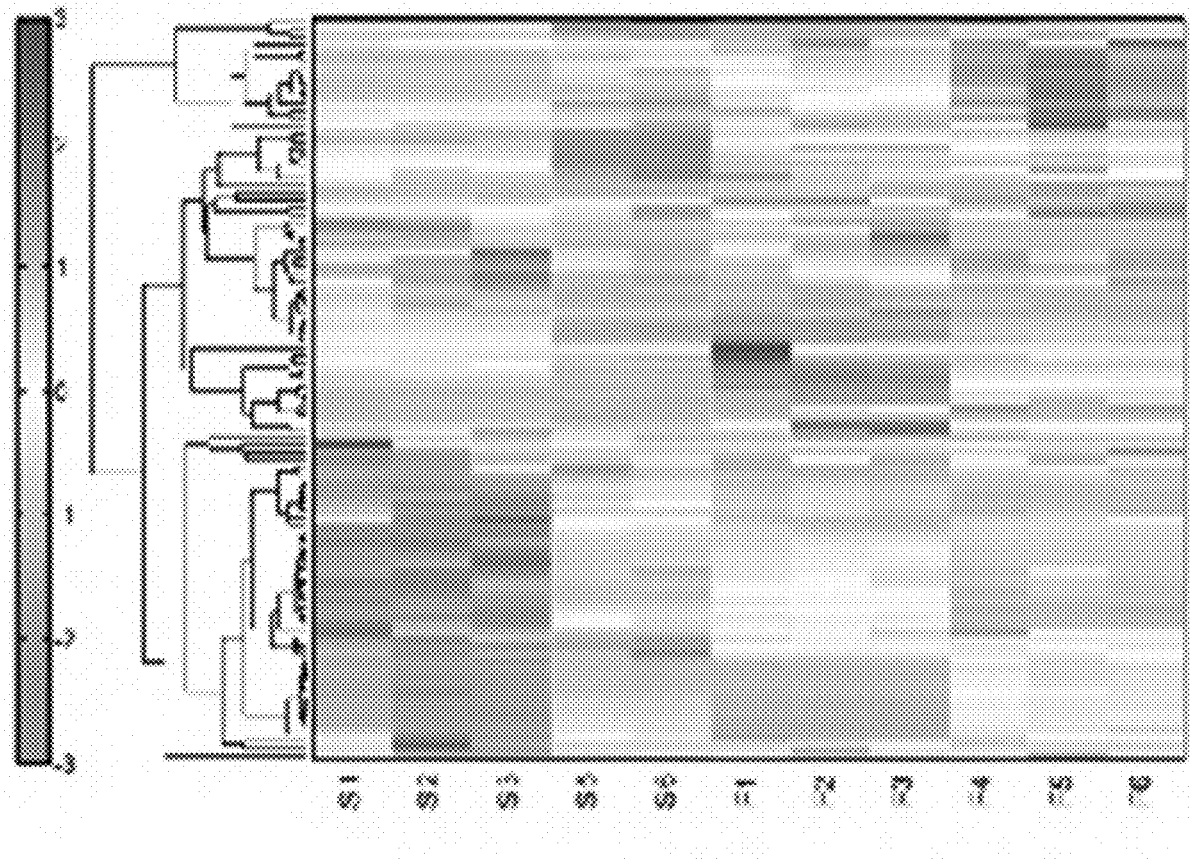
FIG. 7A depicts results from a hierarchical clustering analysis that was conducted in order to compare the overall metabolomic profiles in cells.
Figure 7B:
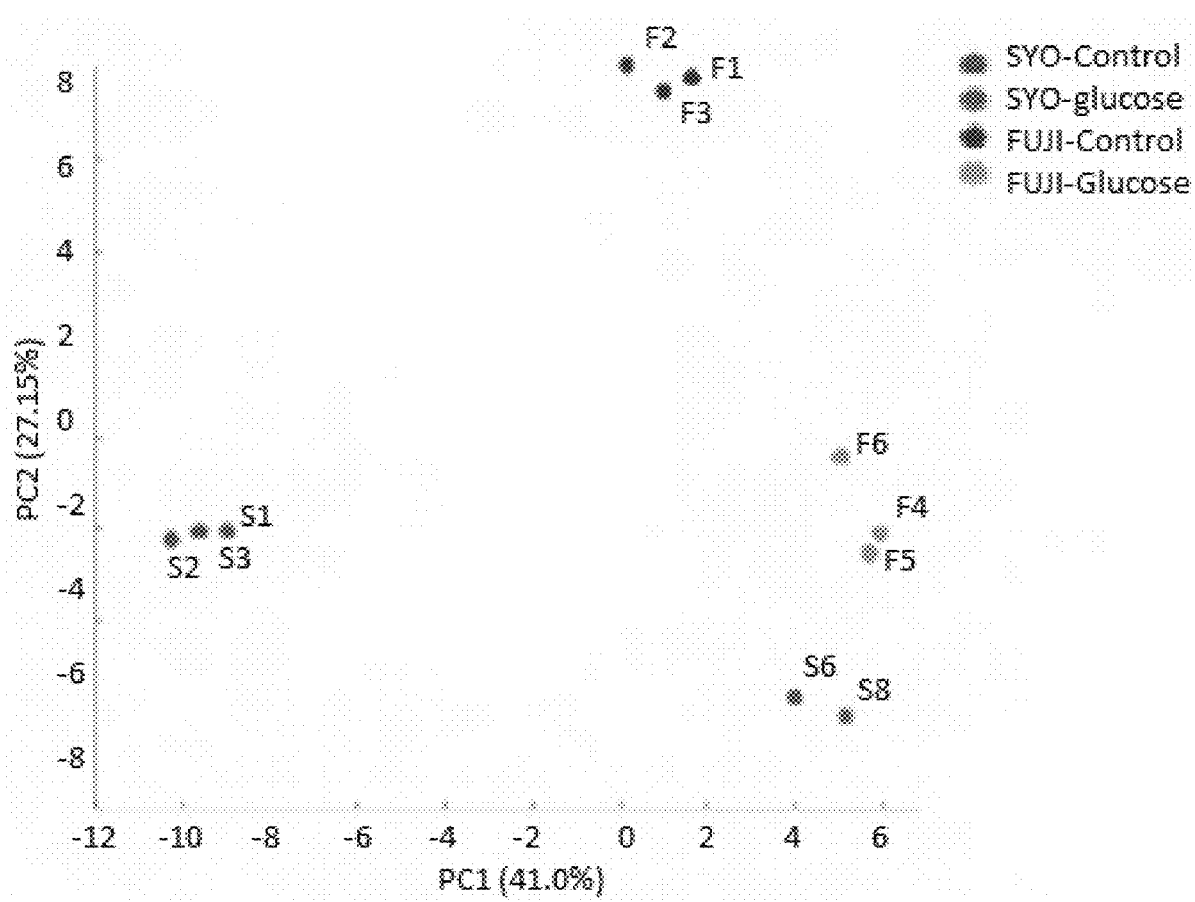
FIG. 7B depicts results from a principal component (PC) analysis that was conducted in order to compare the overall metabolomic profiles in cells.

Example 3. Rapid Flux of Glucose Through Upper Glycolysis and the Pentose Phosphate Pathway In order to better understand the mechanism of cell death, metabolism of glucose and role of ROS in SS, SYO-1 and FUJI cells were subjected to 30 minutes of glucose withdrawal and metabolic quantitative GC-MS mass spectroscopy was performed to determine changes that occur as a result of acute glucose withdrawal. Hierarchical clustering analysis was conducted in order to compare the overall metabolomic profiles in cells (FIG. 7A) and the principal component (PC) analysis was conducted in order to compare the overall metabolomic profiles in cells (FIG. 7B). The data was then examined to identify metabolic pathways that were acutely altered and those that were unaffected.

Figure 8A:
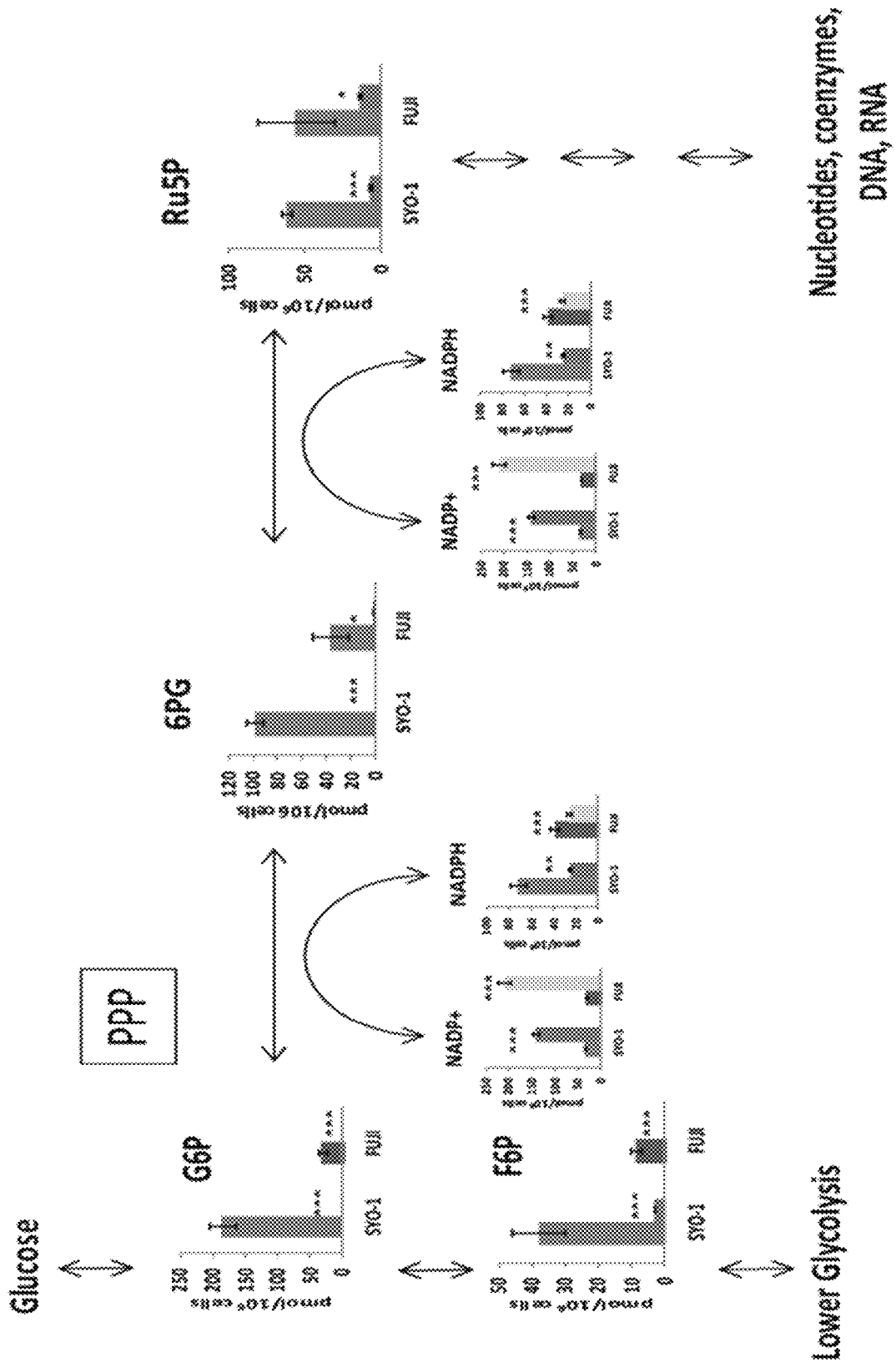
FIG. 8A, FIG. 8B, FIG. 8C, FIG. 8D, FIG. 8E, FIG. 8F, and FIG. 8G depict graphs showing NADPH and glutathione metabolism.

Glucose 6-phosphate (G6P) to ribose 5-phosphate (R5P) conversion is the first and rate-limiting reaction in the pentose phosphate pathway (PPP). G6P is involved in glycolysis, whereas R5P takes part in the PPP; therefore, the glucose 6-phopshate-to-ribose 5-phosphate ratio serves as an indirect parameter to show the significance in the activity of glycolysis or PPP. Both upper glycolysis and the PPP are reliably depleted without a source of glucose, validating the true glucose deprivation condition under which SS was studied (FIG. 8A). The bars/lines represent absolute concentrations of each metabolite in SYO-1 control (blue), SYO-1 (−) glucose (red), FUJI control (green), FUJI (−)glucose (orange), respectively.

Example 4. NADPH and Glutathione Metabolism

Figure 8B:
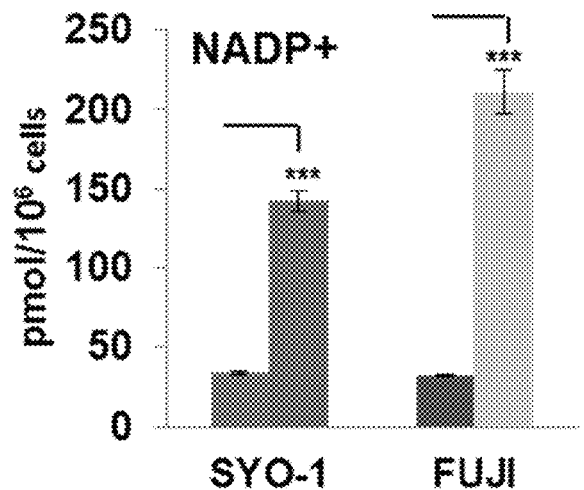
Figure 8C:
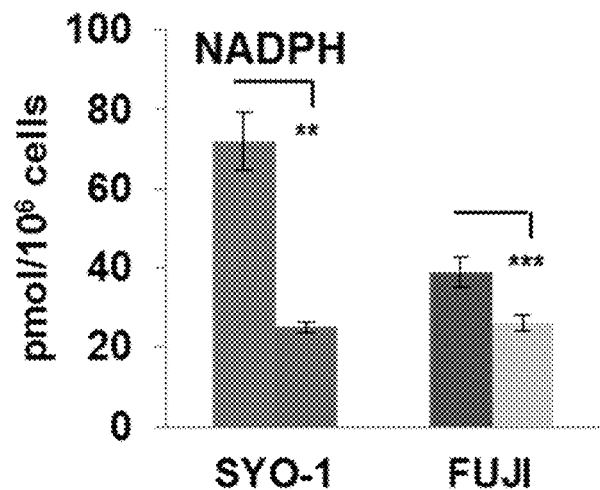
Figure 8D:
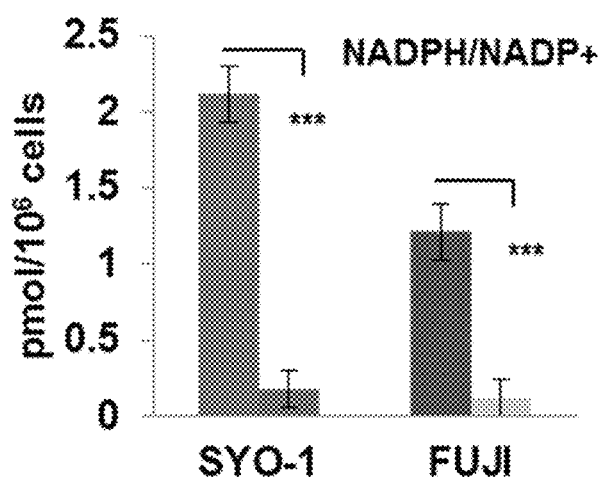
Figure 8E:
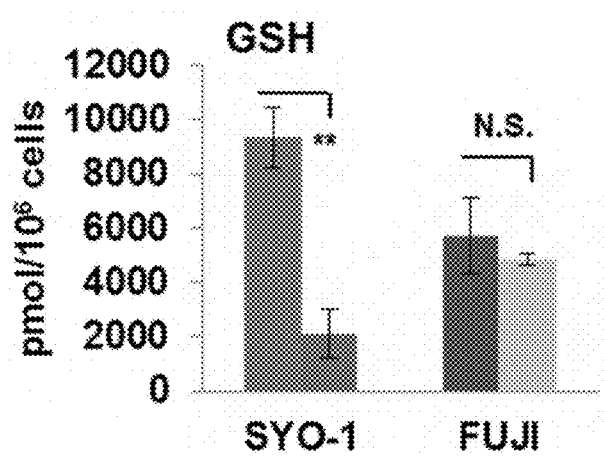
Figure 8F:
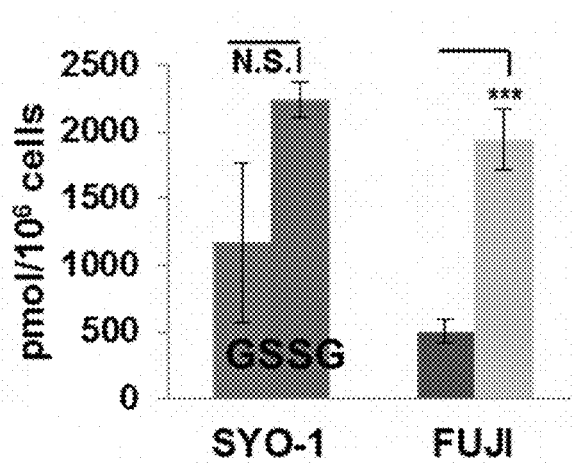
Figure 8G:
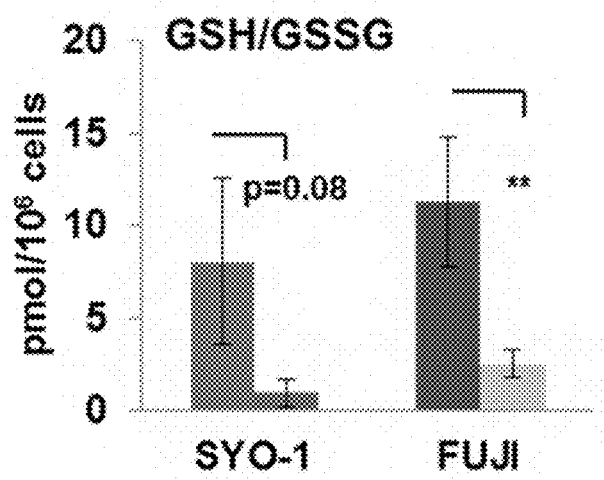

Examination of the redox balance of SYO-1 and FUJI under normal and glucose deprivation conditions revealed a decrease in glutathione (GSH) and statistically significant increase in glutathione disulfide (GSSG), the reduced form of GSH, as well as a statistically significant difference in the ratio of GSH to GSSG (FIG. 8B, FIG. 8C, and FIG. 8D). Glutathione is an established reactive oxygen species (ROS) scavenger and is recycled from its reduced form, GSSG, by glutathione reductase. This reaction requires NADPH, resulting in the formation of NADP+. Under glucose deprivation conditions, NADPH levels are statistically significantly decreased, as is the ratio of NADPH to NADP+(FIG. 8E, FIG. 8F, and FIG. 8G), suggesting that the accumulation of NADP+ with the loss of NADPH and the concomitant accumulation of the reduced form of GSH suggests that SYO-1 and FUJI experience an impairment in glutathione recycling under glucose deprivation conditions.

Example 5. Malic Enzyme 1 Protein Expression is Suppressed in SS

Having established that SS cell lines experience an acute, energetic ferroptotic cell death secondary to ROS accumulation under glucose deprivation, the findings gleaned from the metabolomics analysis under similar conditions were followed up on. Specifically, the quantitative results of the metabolomics in regards to reactions that resulted in production of NADPH were examined. There are three reactions that result in significant NADPH production, two of which are found in the oxidative phase of the pentose phosphate pathway. The rate-limiting reaction of the pentose phosphate pathway, glucose-6-phosphate (G6P) to 6-phosphogluconate (6-PG) via glucose-6-phosphate dehydrogenase (G6PD), and its substrate reaction, 6-PG to ribulose-5-phosphate via 6-phosphogluconate dehydrogenase (6-PGD), both produce NADPH (FIG. 8A). Additionally malic enzyme 1 (ME1), a cytosolic NADP-dependent enzyme which also plays a role in fatty acid synthesis, generates NADPH and performs the oxidative decarboxylation of malate to pyruvate.

Figure 9A:
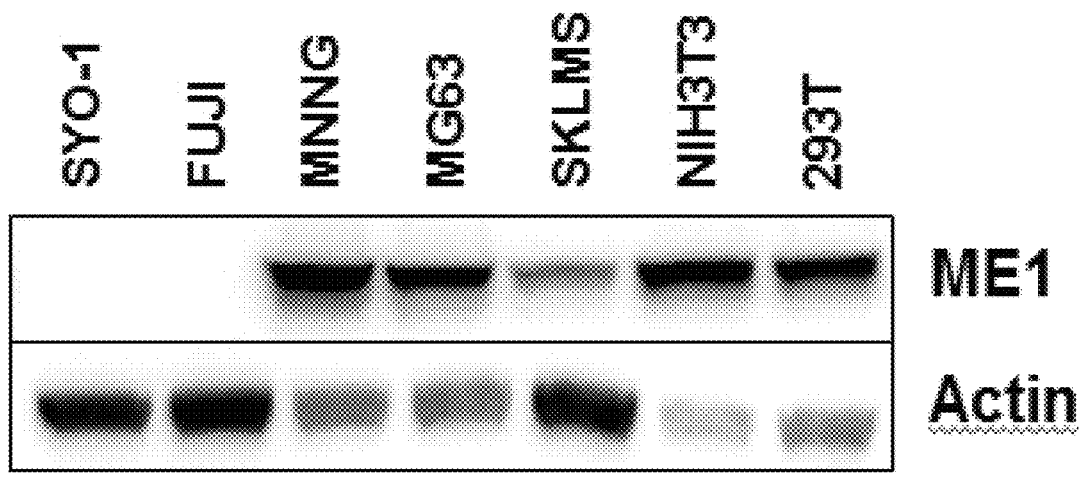
FIG. 9A, FIG. 9B, FIG. 9C, FIG. 9D and FIG. 9E depict immunoblots, graphs and a heat map showing that malic enzyme 1 protein expression is suppressed in SS.
Figure 9B:
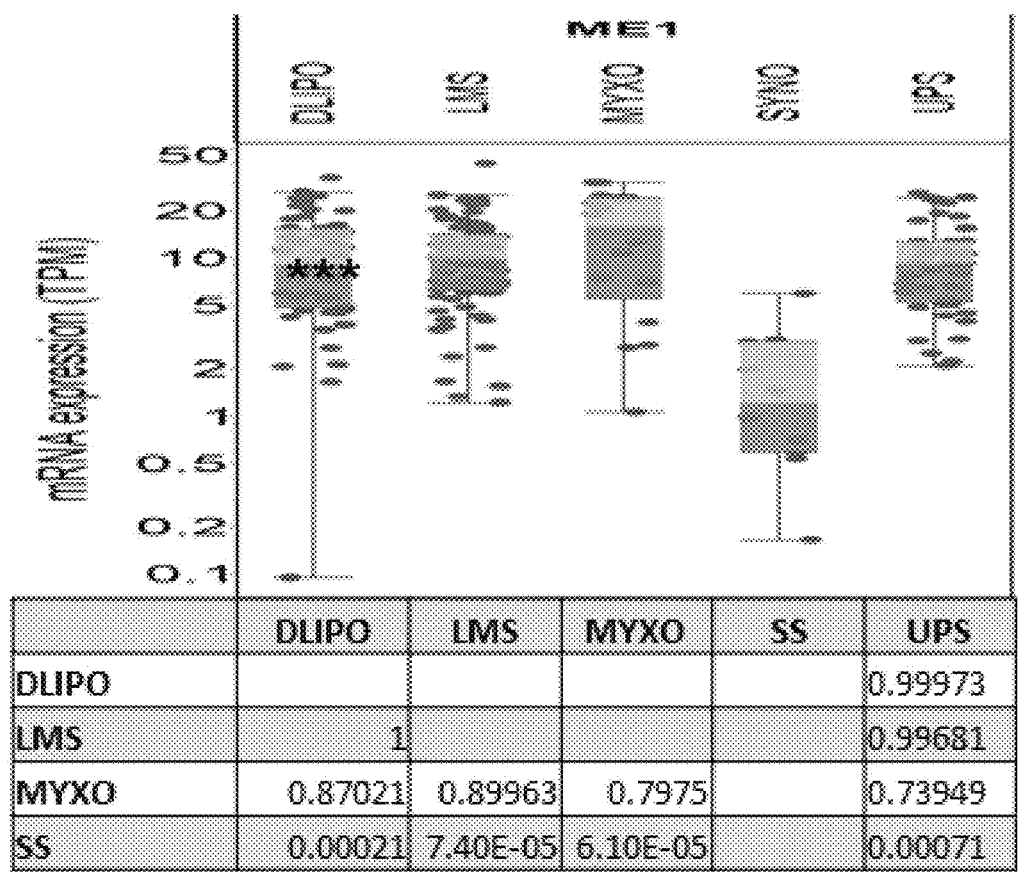
Figure 9C:
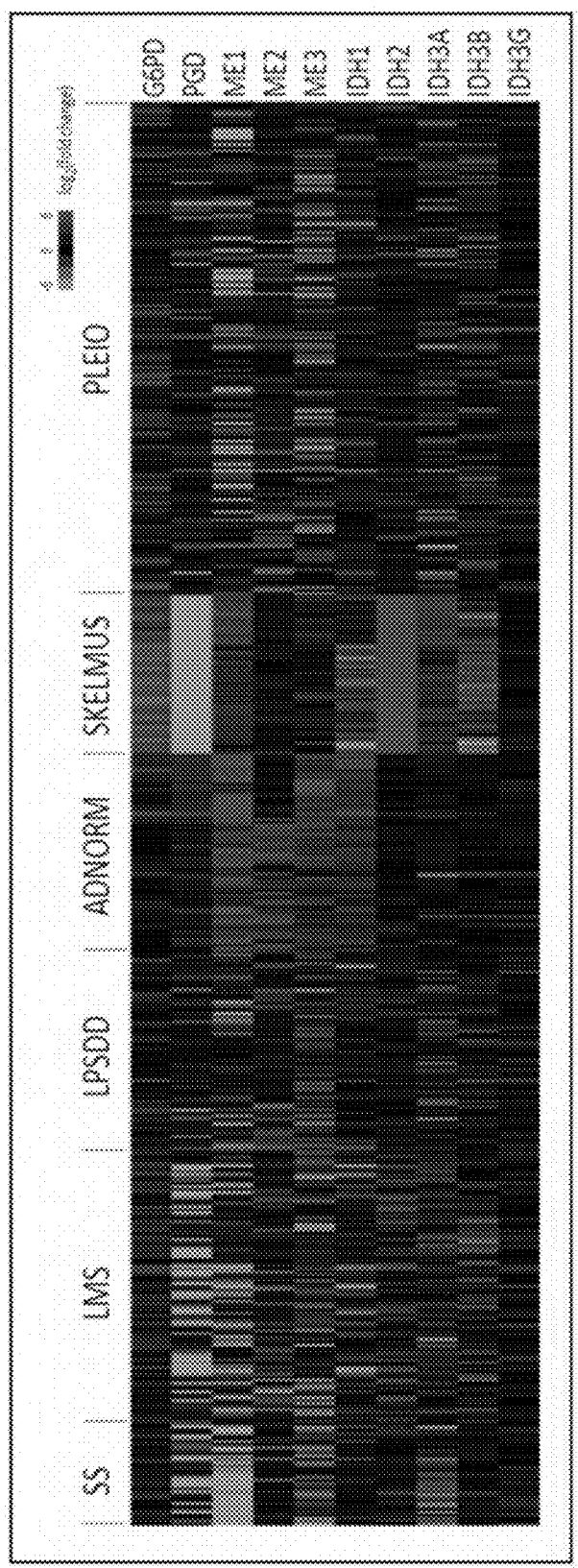
Figure 9D:
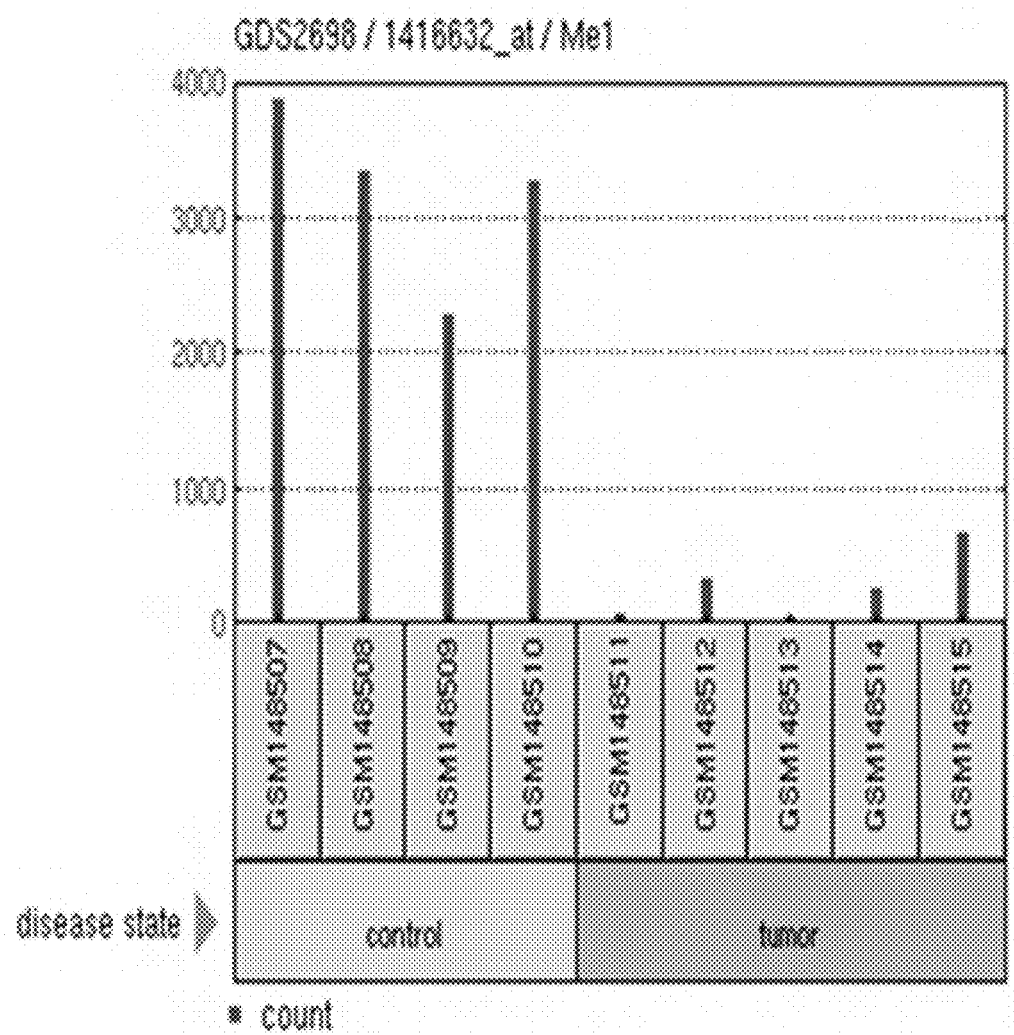
Figure 9E:
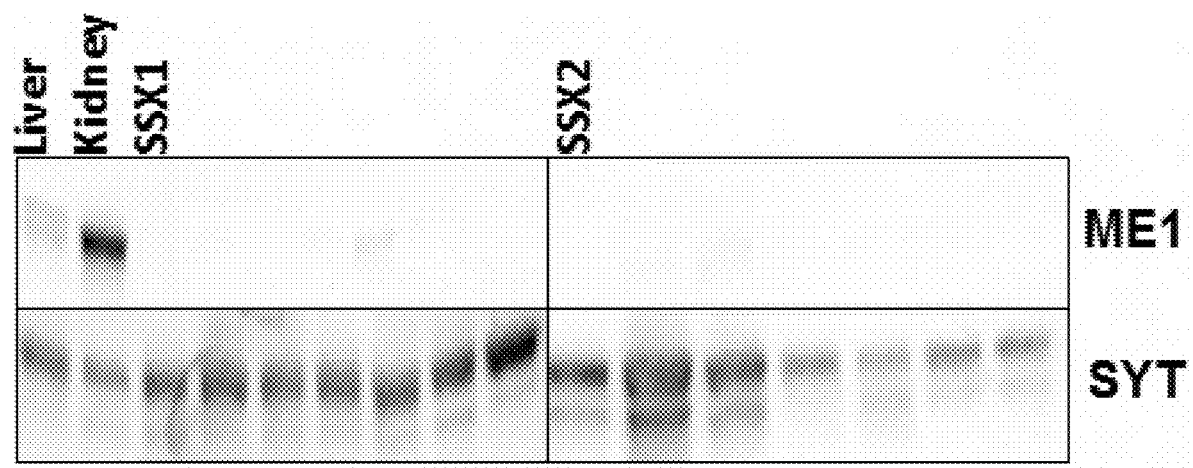
Figure 10A:
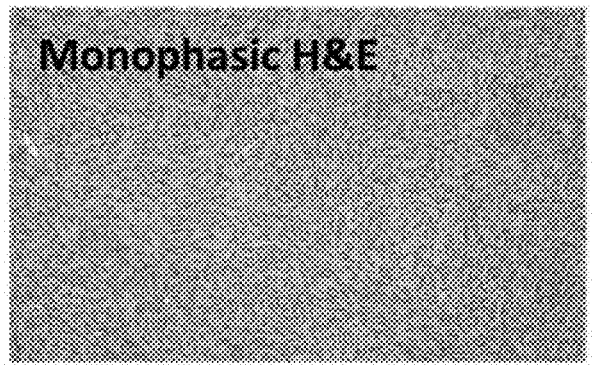
Figure 10B:
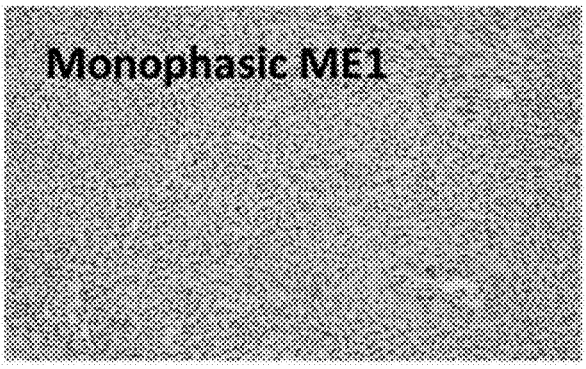
Figure 10C:
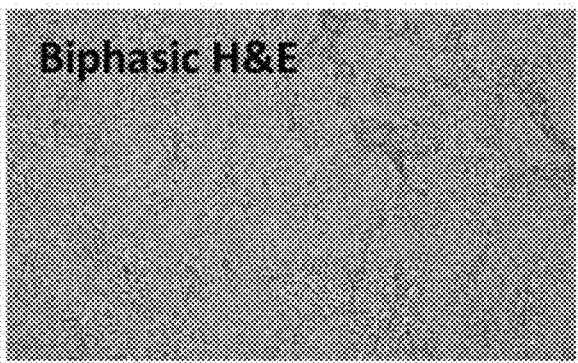
Figure 10D:
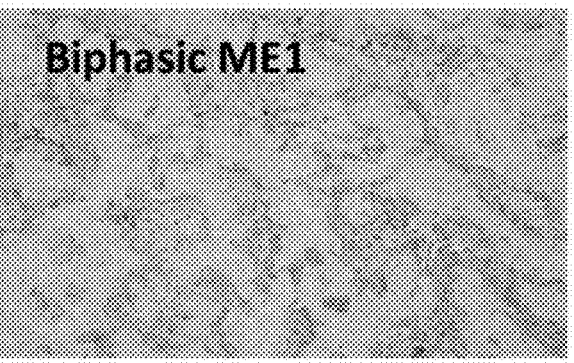
Figure 10E:
Figure 10F:
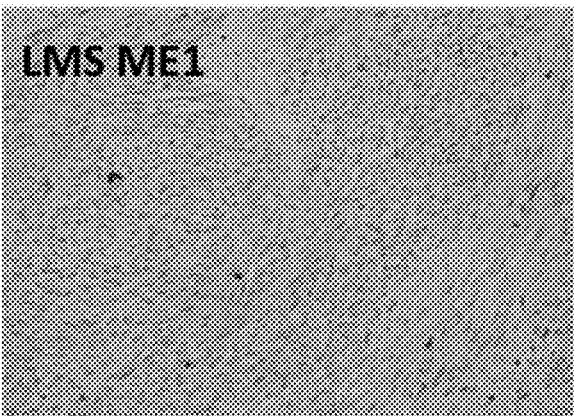

Having established that NADPH depletion is intricately involved with SS cell death in vitro, the expression of cellular NADPH-producers in SS in vivo was determined. In both SYO-1 and FUJI cell lines, the expression of G6PD was stable (FIG. 6), while short hairpin knockdown of G6PD resulted in cell death in SYO-1 and FUJI when compared to MG63 and SKLMS1. However, the expression of ME1 was noted to be absent in both SYO-1 and FUJI when compared to a panel of additional cell lines (FIG. 9A). RNA microarray analysis confirmed a dramatic loss of ME1 expression in 40 SS clinical samples when compared to over 100 leiomyosarcoma (LMS), dedifferentiated liposarcoma, pleiomorphic and undifferentiated sarcomas, normal abdominal adipose tissue, and normal skeletal muscle tissue samples (FIG. 9B). Furthermore, mRNA expression of ME1 in SS is significantly lower than that of dedifferentiated liposarcoma, leiomyosarcoma, myxosarcoma, and undifferentiated pleiomorphic sarcoma per TCGA analysis (FIG. 9C). Investigation into ME1 expression of the SYT-SSX1 and SYT-SSX2 transgenic mouse models revealed a significant decrease in ME1 expression in tumor tissue when compared with the control tissue, mouse muscle (FIG. 9D). Therefore \ tumor lysates from 14 different SYT-SSX transgenic mouse models (7 from SSX1, 7 from SSX2) were examined, which revealed a similar lack of ME1 expression when compared to NIH3T3 cells (embryonic mouse kidney/liver) (FIG. 9E). Finally, 20 primary tissue samples were examined from SYT-SSX break apart proven SS and 20 LMS patient tissue samples. When immunohistochemistry (IHC) of SS clinical samples were analyzed for ME1 expression, monophasic SS demonstrated two patterns. The first, purely monophasic in morphology, was noted in 5/20 samples that were completely negative for ME1. The second pattern appeared to be a "starry sky pattern" where occasional sporadic cells are positive but the majority (99%) are negative, and was noted in 8/20 samples. More interestingly, in biphasic SS tumors, while the sarcomatous portion of the tumor lacks ME1 expression, the biphaisic carcinomatou portion of the tumor is positive for ME1. This suggest that the sarcomatous biphasic and monophaisic SS are negative for ME1 whereas any transition to being biphasic is associated with being positive for ME1 (FIG. 10A, FIG. 10B, FIG. 10C, FIG. 10D, FIG. 10E, FIG. 10F and FIG. 10G).

Figure 11A:
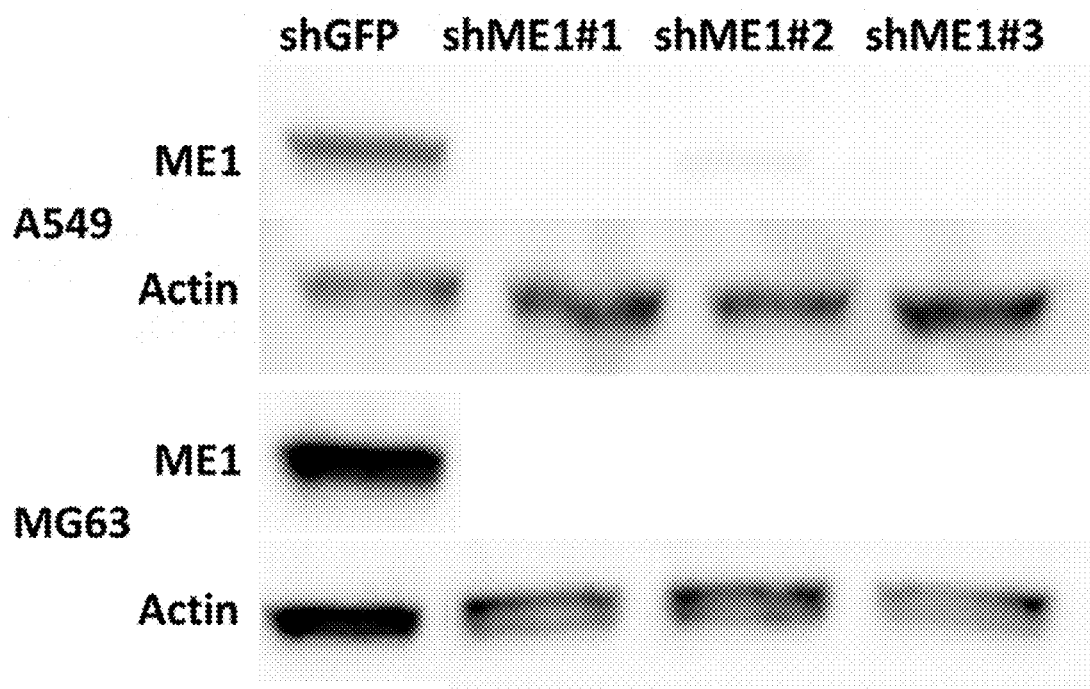
FIG. 11A, FIG. 11B and FIG. 11C depict immunoblots and a graph showing knockdown of ME1.
Figure 11B:
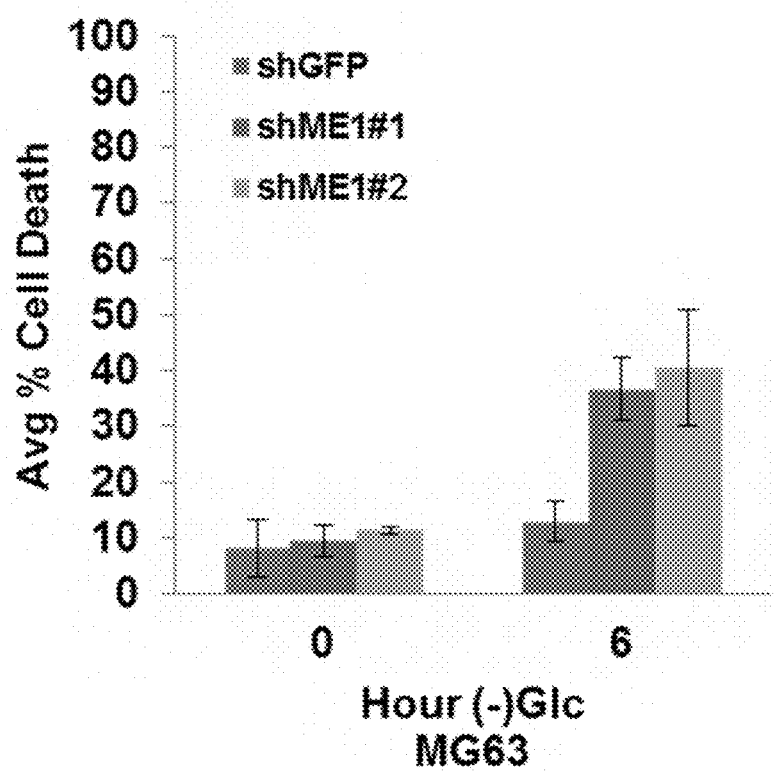

Recognizing that the lack of ME1 in SS cell lines, the SS transgenic mouse model, and patient tumor samples renders these cells particularly sensitive to glucose deprivation, ME1 was knocked down in cell lines with stable ME1 expression. In MG63, an osteosarcoma, all constructs displayed marked ME1 knockdown; also shown with marked ME1 knockdown in A549 (lung carcinoma) (FIG. 11A). With effective knockdown of ME1, marked sensitivity to glucose deprivation over an acute time period was conferred to these cell lines with inherent ME1 expression (FIG. 11B). This conferred phenotype confirms that ME1 is a necessary and vital source of NADPH used to maintain cellular redox balance.

Figure 11C:
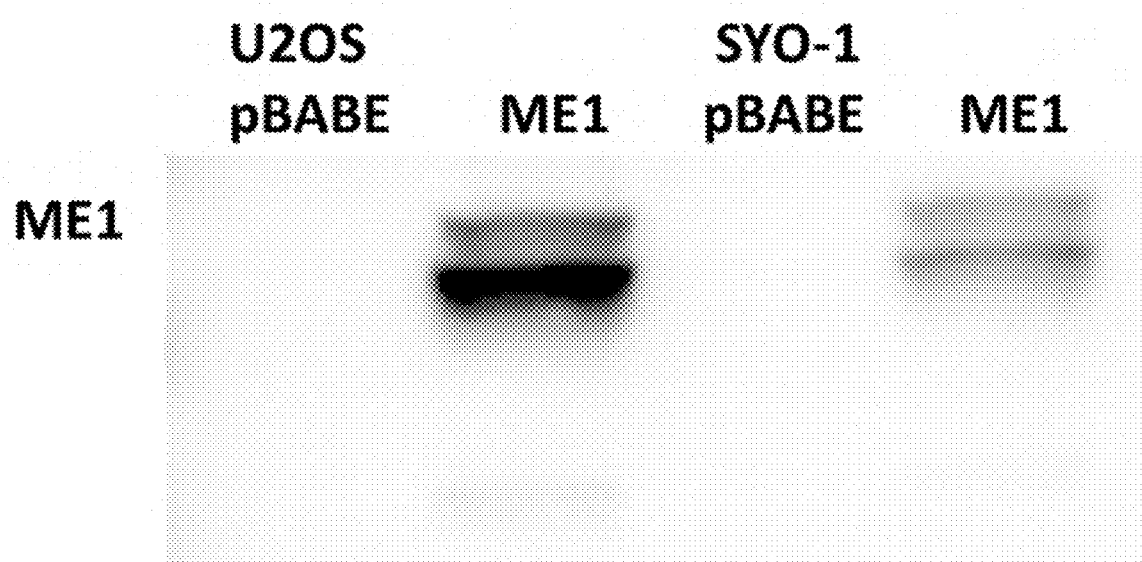

Intending to investigate the potential restorative effects of overexpressing ME1 in SS lines, SYO-1, and FUJI, ME1 was stably overexpressed. However, after confirming expression of an ME1 construct via transfection in SYO-1 and FUJI, a ME1-positive SS cell line was unable to successfully propagate. Introduction of the ME1 construct into SS cell lines via infection was uniformly lethal. FIG. 11C depicts ME1 expression via viral vector.

Figure 13A:
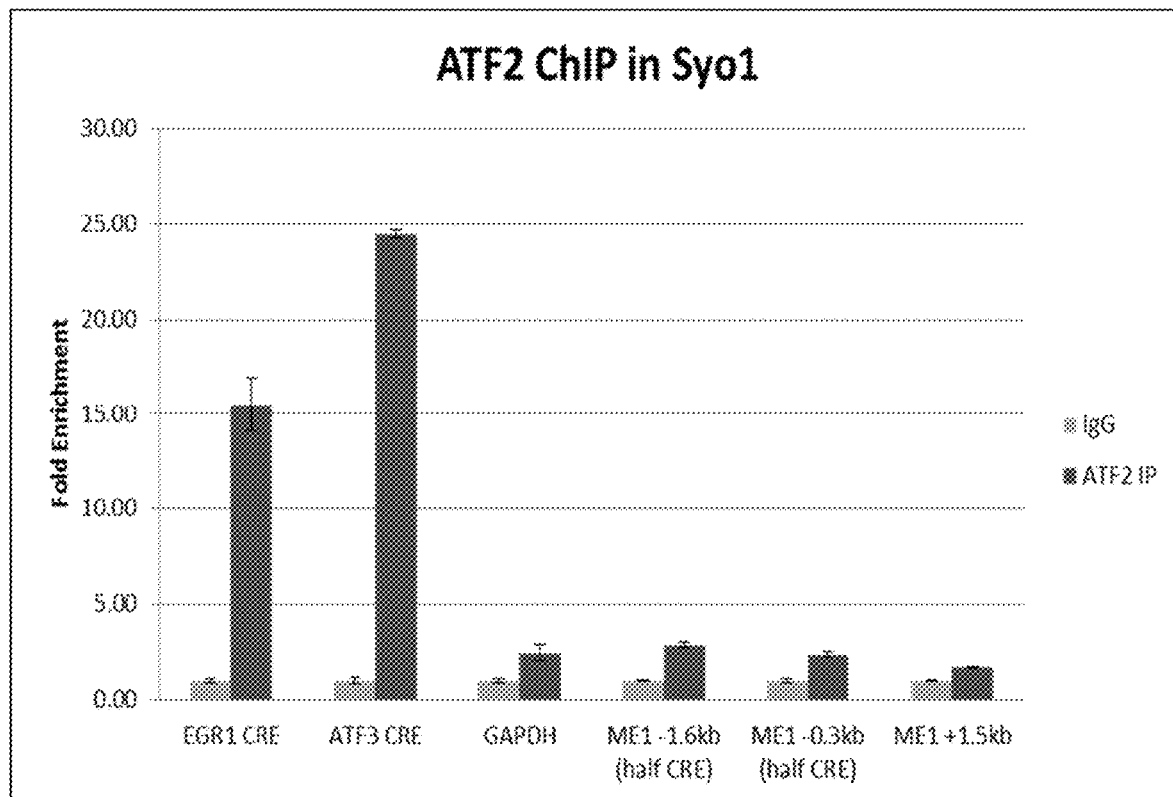
FIG. 13A and FIG. 13B depict a graph and polymerase gel showing that ME1 is silenced by methylation.
Figure 13B:
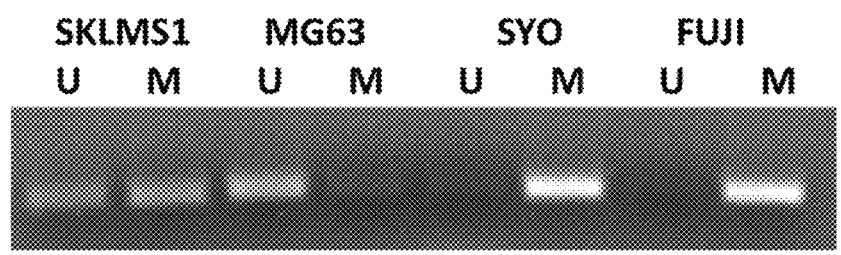

Analysis of the SYT-SSX2 fusion protein by ChIP revealed that the translocation is not associated with the ME1 promoter; the translocation indirectly suppresses ME1 (FIG. 13A). Methylation-specific PCR of the ME1 promoter revealed that, in SYO-1 and FUJI, there is heavy methylation of the ME1 promoter when compared to SKLMS-1 and MG-63, which each show partial methylation of the ME1 promoter (FIG. 13B).

Example 6. Inhibition of G6PD Leads to Cell Death

Figure 6:
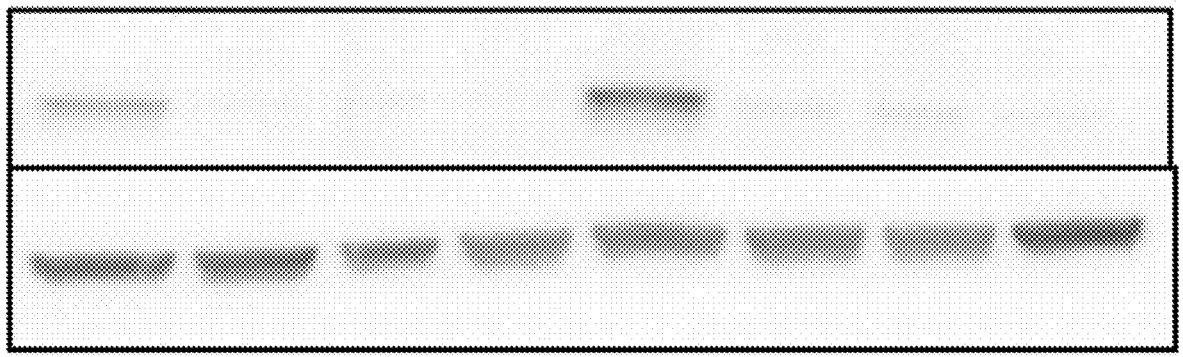
FIG. 6 depicts an immunoblot showing that in both SYO-1 and FUJI cell lines, the expression of G6PD was stable.
Figure 12A:
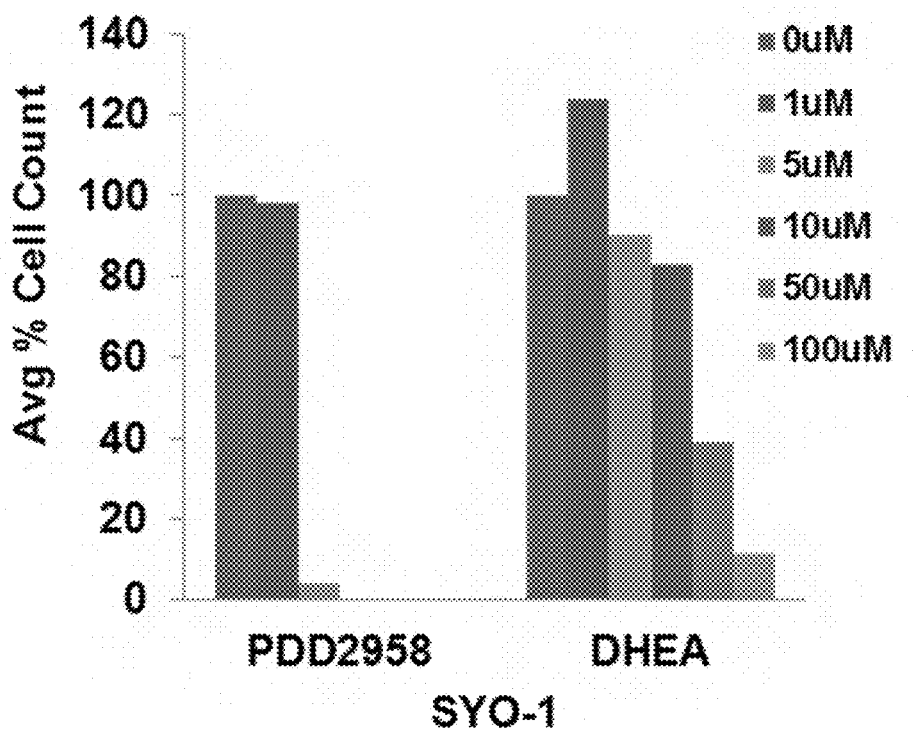
Figure 12B:
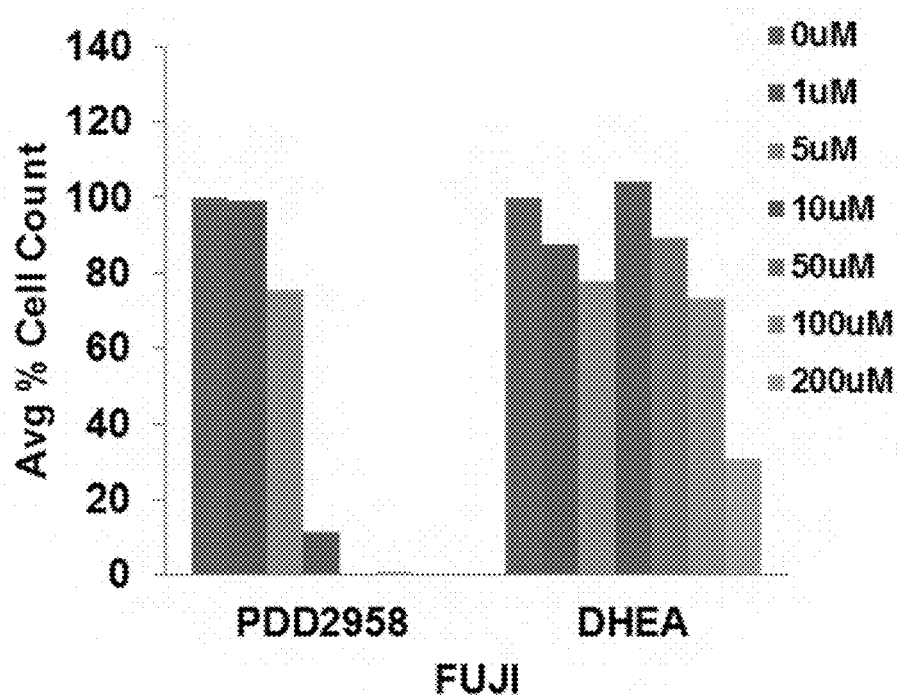
Figure 12F:
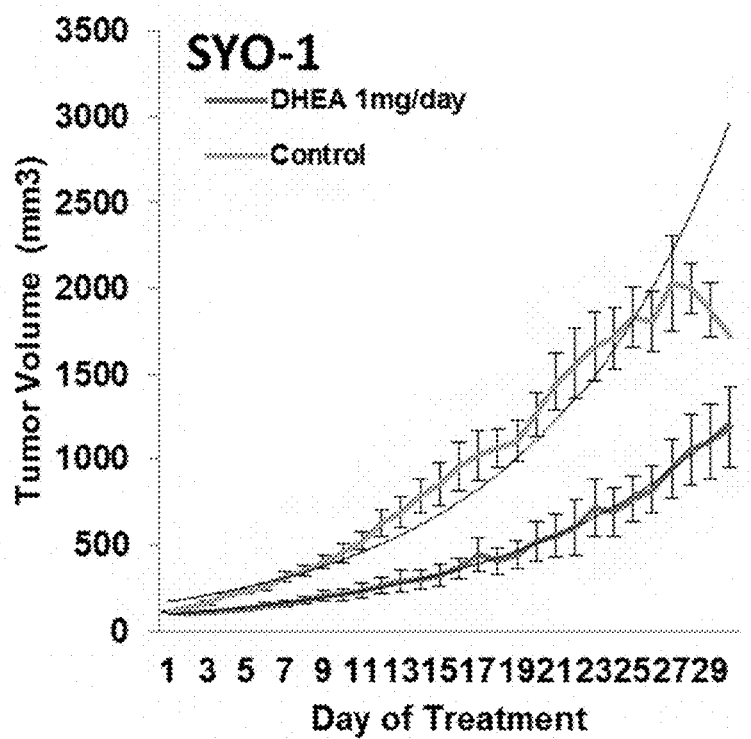
Figure 12G:
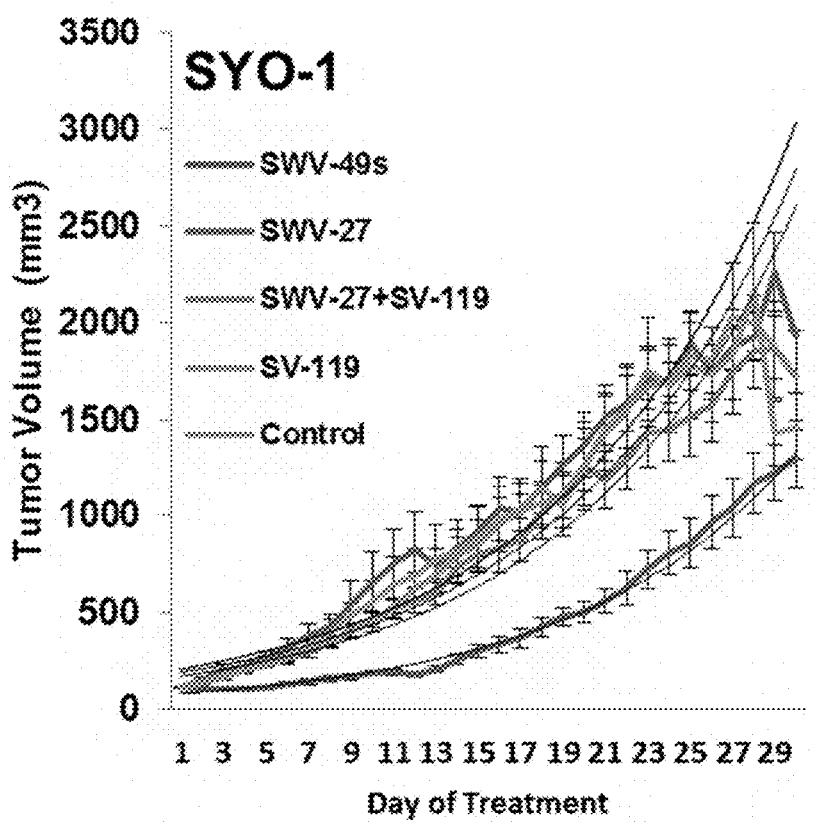
Figure 12H:
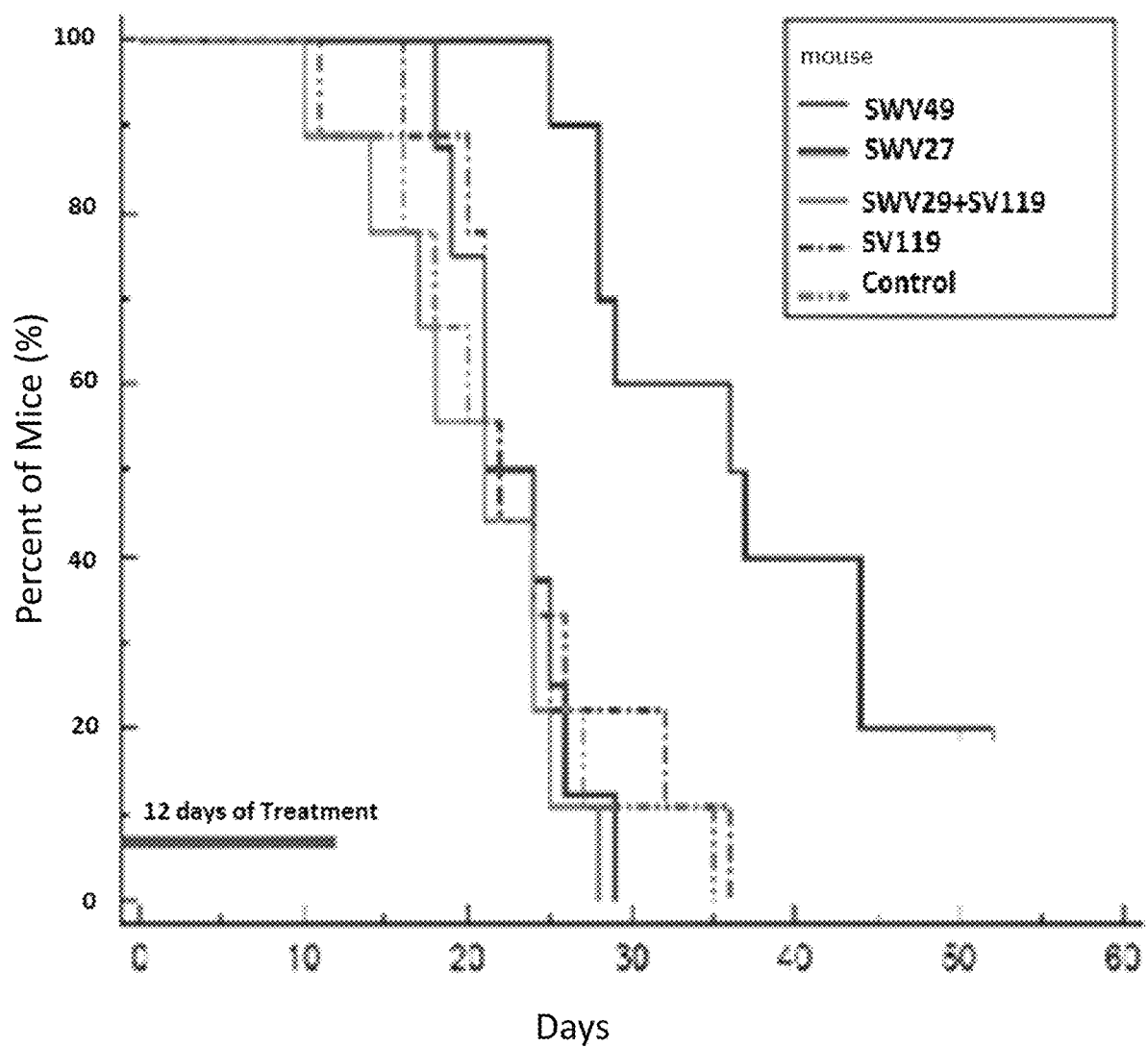

Recognizing that the lack of ME1 in SS results in the dependence upon the pentose phosphate pathway for NADPH production, it was initially established that G6PD expression in both SYO-1 and FUJI were stable (FIG. 6). Additionally, when G6PD was knocked down in these SS cell lines, significant cell death was noted, to the point that standard tissue culture experiments were not able to be performed. When treated with dehydroepiandrosterone (DHEA), a G6PD inhibitor, over a course of 48 hours, both SYO-1 and FUJI displayed varying but significant cell death (FIG. 12A, FIG. 12B). When treated with a range of DHEA analogs, PDD2958 displayed a 2 log improvement in the IC50 when compared with DHEA itself (FIG. 12A, FIG. 12B). The in vitro data was mirrored in vivo when SYO-1 was grafted into a murine model, where a dramatic decrease in tumor size was noted with a dose of 1 mg/day of DHEA for 12 days, a dose and regimen that was well-tolerated by the murine model and persisted after cessation of treatment (FIG. 12F). Recognizing that testosterone is a downstream derivative of DHEA, it was determined that there is negligible expression of the androgen receptor in our SS cell lines, eliminating the role of androgen biology in the cell death noted with DHEA treatment in vitro.

Example 7. Sigma2-Erastin Inhibits Tumor Growth In Vivo

Erastin has been established as a small molecule inducer of ferroptosis, and it has been previously established that application of erastin results in depletion of reduced glutathione (GSH) and oxidized glutathione (GSSG). This, in turn, induces the formation of ROS, resulting in an oxidative form of cell death. Treatment of SYO-1 and FUJI cell lines with erastin resulted in significant cell death at 24 hours when compared with SKLMS-1 and MG-63 (FIG. 12C, FIG. 12D, and FIG. 12E). When treated with sigma-2 erastin, a form of erastin that binds the sigma-2 ligand for rapid cell internalization, the IC50 in SYO-1 and FUJI was significantly improved when compared to erastin, the combination of erastin and the sigma ligand, and the sigma ligand alone (FIG. 12C, FIG. 12D, and FIG. 12E). In the in vivo murine model, treatment with sigma erastin mirrored that of DHEA, resulting in a significant slow in tumor growth when compared to the control vehicle, sigma ligand, sigma ligand and erastin, and erastin arms of the experiment (FIG. 6E, FIG. 6F).

Methods for Examples 1-7

Cell Lines:

The SKLMS1, MG63, MNNG, RKO, HT-1080 and SKUT1 cell lines were cultured at 37° C. in 5% $CO_2$, in Modified Eagle Medium (MEM) (Life Technologies, Grand Island, N.Y.) supplemented with 10% FBS and Penicillin-Streptomycin 100× (10,000 U/mL) (Life Technologies, Grand Island, N.Y.), FUJI, A549, HCC2998, H522, and H266 in RPMI Medium 1640 (Life Technologies, Grand Island, N.Y.) supplemented with 10% FBS and Penicillin-Streptomycin 100× (10,000 U/mL) (Life Technologies, Grand Island, N.Y.); SYO-1 in Dulbecco's Modified Eagle Medium (DMEM) (Life Technologies, Grand Island, N.Y.) supplemented with 10% FBS and Penicillin-Streptomycin 100× (10,000 U/mL) (Life Technologies, Grand Island, N.Y.), as well as used as control in glucose and glutamine deprivation experiments. Glucose and Glutamine deprivation experiments used glucose or glutamine free Dulbecco's Modified Eagle Medium (Product numbers 11966-025 and 11960-044 respectively) (Life Technologies, Grand Island, N.Y.), with 10% dialyzed FBS and Penicillin-Streptomycin 100× (10,000 U/mL) (Life Technologies, Grand Island, N.Y.). Cells were regularly passaged with 0.05% Trypsin/EDTA (500 mg/ml Trypsin, 200 mg/ml EDTA) (Life Technologies, Grand Island, N.Y.). The leiomyosarcoma lines (SKLMS1 and SKUT1), the osteosarcoma line (MNNG), the colorectal carcinoma (HCT116), the lung adenocarcinoma cell lines (A549), SYO-1, FUJI, MG63, U2O2, RKO, HT-1080, HCC2998, H522, and H226 were all obtained from ATCC (Manassas, Va.).

Western Blot Analysis.

Cell pellets were collected, lysed with RIPA buffer, sonicated and incubated on ice for 30 minutes. Samples were then centrifuged for 15 min, at 4° C. and supernatants were collected. For analysis of xenograft and transgenic mouse tumor protein expression, tumor slices were lysed in RIPA buffer for 30 minutes and homogenized using Axygen PES-15-B-SI pestles before sonication and centrifugation. 40 µg of protein lysate were added per sample, diluted in millipure $H_2O$ to 20 µL, and diluted further with 2×SDS-PAGE Sample Buffer. Samples were boiled at 100° C. for 5 minutes and ran through an SDS-PAGE gel. Samples were electrotransfered onto 0.2 µm PVDF membranes. Membranes were blocked with 5% milk in 1×5% PBS-Tween for 30 minutes at room temperature. Primary antibodies were diluted in 5% milk in 1×5% PBS-Tween incubated on a rocker at 4° C. overnight. For analysis of GLS expression, membranes were incubated with primary antibody for 4 hours at room temperature. After primary antibody incubation, membranes were washed three times in 1×PBS-Tween (5 minutes each). Ten mL of 5% PBS-Tween was added to each blot along with species specific HRP conjugated secondary monoclonal antibodies at a concentration of 1:10,000 and incubated for 1 hour. The light chain specific secondary antibody was used in the analysis of the xenografts to control for mouse cells harvested with the tumor. Filters were washed 3 times in 1×PBS-Tween (5 min each). SuperSignal West Dura Extended Duration Substrate Kit (ThermoScientific) was used for visualization. Unused lysates were stored at −20° C. for short-term storage, or −80° C. for long term storage.

Cell Counting Experiments and Propidium Iodide FACS.

During the routine cell culture splitting procedure, cell lines were plated in 6 well plates at 200,000 cells in 2 mL media. Samples were incubated at 37° C. for duration of experiment. Samples were washed with PBS and detached with 0.05% Trypsin/EDTA. Aliquots were diluted 1:2 with Trypan Blue (Sigma) and a viable cell count was obtained using a hemacytometer. For glucose and glutamine deprivation experiments, 200,000 cells were plated in standard media and incubated overnight. Samples were washed 3 times with 1×DPBS (Gibco), and the media was changed to DMEM (control samples) or glucose/glutamine free DMEM (experimental samples). Cell counts were taken as previously described at 2, 4, 6, and 8 hours after the media was changed, and normalized to cell counts taken from growth samples counted at the time the media was changed.

For FACS analysis, cell lines were plated at 200,000 cells per well, and incubated in various culture conditions. Media was collected in a FACS tube and samples were washed with PBS. The PBS was transferred into the FACS tube, and 0.5 mL 0.05% Trypsin/EDTA was added to each well. Samples were incubated for 5 minutes at 37° C., and diluted with 0.5 mL complete media before being transferred to the FACS tube. Wells were washed once with PBS, transferred to the FACS tube, and centrifuged at 800 g for 5 minutes at room temperature. The supernatant was aspirated off, and pellets were resuspended in 200 µL PBS (unstained control samples used for gating) or 200 µL of 1 µg/mL propidium iodide dissolved in PBS. Samples were run on a FAScan instrument and fluorescence analyzed on the Blue FL2 channel. Data was further analyzed using FloJo software.

Metabolomic Analysis.

SYO-1 and FUJI were plated in 10 cm dishes in appropriate media at the time of plating. Prior to metabolite extraction, the plates were washed three times with PBS then incubated in DMEM (control plates) and glucose-free DMEM for 30 minutes. Metabolite samples were then extracted per HMT Metabolite Extraction Method for Adherent Cells for the control and glucose-free samples. A separate 10 cm dish of each cell line and treatment condition was then counted via trypan blue exclusion to provide a number of viable cells to allow for normalization of metabolite concentrations.

shRNA Mediated Knockdowns.

Knockdown of GLS via shRNA was completed by cloning of the hairpin into the pLKO vector. Lipofectamine 2000 was used for plasmid transfection. Lentivirus was produced in HEK293T cells by co-transfection with VSVG and deltaR plasmids. Viral supernatants were harvested and cells infected in the presence of 5 µg/ml polybrene. Infected cells were selected for by culturing in puromycin, at 1.5 µg/mL for SKLMS1 and SKUT1 cell lines, and 2.5 µg/mL for the SKMEL2 cell line. The targeting sequence for the shGFP construct is GCGCGATCACATGGTCCTGCT (SEQ ID NO:1), shGLS #1 is GGATTCAGTAATGCAACGTTTCAGT (SEQ ID NO:2), and shGLS #2 targeting sequence is GCCCTGAAGCAGTTCGAAATA (SEQ ID NO:3).

Xenograft Studies.

BALB/c mice were inoculated subcutaneously on the right flank with 1×10$^6$ SKMEL2 shGFP, shGLS #1, or shGLS #2 cells in 33.333% Matrigel (BD Biosciences). When tumors reached approximately 100 mm$^3$, mice were injected with ADI-PEG20 intramuscularly every 3 days. Animals treated with ADI-PEG20 were given 320 IU/m$^2$ (Feun et al., 2012). Tumors were measured every other day by caliper, and tumor volumes were calculated by ½× (length×width$^2$). After treatment ended, mice were sacrificed and tumors were harvested for western blot analysis.

Trypan Blue Exclusion Assay.

Cell viability was determined in tissue culture experiments by the trypan blue dye exclusion test. For the evaluation of glucose deprivation, cell lines were plated in a 6-well format at 200,000 cells per well on day 1. SYO was cultured and plated in Dulbecco's Modified Eagle Medium (DMEM) with 10% FBS and penicillin/streptomycin (include additional glucose concentration), which FUJI was cultured in RPMI medium with 10% FBS and penicillin/streptomycin. The following day, glucose-containing media was removed, and each well was washed with 1-2 mL of phosphate buffered saline (PBS) three times to ensure elimination of residual glucose. Glucose-free media was then replaced in each well for the duration of the experiment. At the end point, the glucose-free media was removed and each well washed with 1 mL of PBS. One-half milliliter of trypsin 0.05% was then applied to each well, later aggressively resuspended in 0.5 mL of media for a total cell volume of 1 mL. Twenty microliters of each well was then counted via hemocytometer, excluding those non-viable cells that were positive for trypan blue uptake and/or fragmented.

Propidium Iodide Staining/Flow Cytometry Analysis.

For the evaluation of glucose deprivation alone and under additional conditions, cell lines were plated in a 6-well format at 200,000 cells per well on day 1. SYO was cultured and plated in Dulbecco's Modified Eagle Medium (DMEM) with 10% FBS and penicillin/streptomycin (include additional glucose concentration), which FUJI was cultured in RPMI medium with 10% FBS and penicillin/streptomycin. The following day, glucose-containing media was removed, and each well was washed with 1-2 mL of phosphate buffered saline (PBS) three times to ensure elimination of residual glucose. Glucose-free media was then replaced in each well for the duration of the experiment. At the end point of the experiment, media was removed from each well independently and collected into flow cytometry tubes. Each well was washed with 500 mircoliters (uL) of PBS independently and collected. 500 uL of trypsin 0.05% was applied to each well and incubated at 37 degrees C. for 5 minutes. After incubation and cell dissociation, 1.5 mL of glucose-containing media was added to each well, aggressively resuspended, and independently collected into individual tubes. An additional 500 uL wash of PBS was then applied to each well and collected into the flow cytometry tube. The tubes were then centrifuged at 800 g for 5 minutes at room temperature. A small cell pellet was recognized and the supernatant media gently siphoned from each tube. Two hundred microliters of propidium iodide at 1 ug/mL concentration was then used to resuspend the cell pellet and allowed to incubate while covered for 10 minutes. Samples were then ran and fluorescence analyzed via Blue FL2 channel on a FAScan instrument. One PI-free unstained sample was provided for each cell line to allow for proper gating. A positive control was developed as necessary for each experiment using treatments reliably established within the lab to result in cell death. FACS analysis was performed with a Becton Dickinson FACScan (BD Instruments, San Jose, Calif.) and FlowJo X (FlowJo, LLC, Ashland, Oreg.).

Metabolomic Analysis.

SYO and FUJI cells were plated in a 10 cm dish at 4 million cells per sample in quadruplicate on day 1. On day 2, glucose-containing media was removed from each plate, and each plate was washed with 10 mL of phosphate buffered saline (PBS) three times to ensure elimination of residual glucose. Ten milliliters of glucose-containing media was replaced in the control plates while glucose-free media was added to each treatment plate for a duration of 30 minutes. Metabolite samples were then extracted per HMT Metabolite Extraction Method for Adherent Cells in triplicate for the control and glucose-free samples. The remaining 10 cm dish of SYO and FUJI cells were then counted via trypan blue exclusion to provide a number of viable cells to allow for normalization of metabolite concentrations.

Assessment of ROS Accumulation.

SYO and FUJI were plated in a 96-well format at 10,000 cells/well on a clear/black microplate on day 1. The following day, a 100 mM stock solution of 2',7'-dichlorodihydrofluorescein diacetate (H$_2$DCFDA) was prepared in sterile DMSO and stored in a light-protected fashion at −20° C. Cells were then washed twice with 100 uL of warmed HBSS-glucose, with 50 uL of HBSS-glucose left remaining in each well. Control wells without H$_2$DCFDA were replaced with 50 uL of DMSO with HBSS-glucose while the remainder of the wells were replaced with HBSS-glucose and H$_2$DCFDA at a final concentration of 20 uM. The plate was incubated at 37° C. for 1 hour in a light-protected fashion. All wells were then washed three times with 100 uL HBSS-glucose. Media was replaced per indicated condition in both H$_2$DCFDA-incubated and H$_2$DCFDA-free wells: HBSS-glucose, HBSS-glucose free, HBSS-glucose and NAC 10 mM, HBSS-glucose free and NAC 10 mM. A standard plate reader was set for a kinetic assay read of a wavelength of 485 excitation and 530 emission. Plate readings were collected every minute for 60 minutes and analyzed using H$_2$DCFDA-free wells as a baseline for fluorescence readings. Average fluorescence was calculated for each well and plotted over the 60 minute duration of the experiment.

Cell lines were plated in a 6-well format at 20×10$^4$ on day 1. The following day, the media was suctioned from each well and replaced with DCF 10 uM in 1×PBS and allowed to incubate at 37° C. for 30 minutes. Wells were then washed with 1×PBS twice and incubated under glucose-free conditions for 15 and 30 minutes. Wells were then harvested for FACS analysis as described above and resuspended in 400 uL of 1×PBS and immediately analyzed or stored at 4° C. FACS analysis was performed with a Becton Dickinson FACScan (BD Instruments, San Jose, Calif.) and FlowJo X (FlowJo, LLC, Ashland, Oreg.).

Immunohistochemistry.

FFPE slides were deparaffinized by incubation at 65° C. for one hour, rehydrated, and incubated in 3% hydrogen peroxide for 10 minutes to block endogenous peroxidase. After washing, slides were heated in antigen unmasking solution and allowed to cool to room temperature. Primary antibody (1:100 malic enzyme 1, Abcam, ab97445) was applied to each slide and incubated overnight at 4° C. After washing, biotinylated secondary antibody (1:100 goat anti-mouse, Vector Laboratories Inc BA-9200) was applied and incubated at room temperature for 30-40 minutes. After washing, ABC complex ( ) was applied and incubated for 30 minutes. DAB was then applied and allowed to incubate 30-60 minutes. Slides were then immediately counterstained with hemotoxylin 1 ( ) and mounted.

In Vivo Experiment.

Sixty nude athymic mice (Nu/J homozygous Cat#002019, The Jackson Lab) were xenografted with 1×10^6 SYO-1 cells that had been resuspended in 1×PBS 30% Matrigel (Corning, Inc., Cat# CB-40234). Mice were anesthetized with 1-2% isofluorane and injected at the left flank. The mice were observed until each tumor size was 100 mm3 by caliper measurement, at which point each individual mouse began daily injections of DHEA 1 mg/30 uL ( ), SWV-49s 3.75 mM, SWV-273.75 mM, SV-119 3.75 mM, SWV-27/SV-119 3.75 mM, or control vehicle Cremiphor. All agents were suspended in Cremiphor. Treatment or placebo injections continued for a total of 12 days. Daily caliper and weight measurements for a total of 30 days were undertaken for each cohort. Mice were sacrificed appropriately by " " guidelines and after the conclusion of the in vivo experiment.

NAD(P)H Extraction for LCMS.

ASYO-1 and FUJI cells were plated and then incubated with the tracer glucose concentration at 10 mM. After incubation, the media was removed and the cells washed once with HPLC grade water. All water was then removed and metabolism quenched with liquid N2, then 200 uL of extraction buffer per six well was added. Cells were then scraped, transferred to a microtube then centrifuged. Fifty microliters of sample was then transferred to a polypropylene vial, capped, and stored on ice while awaiting LCMS. LCMS was performed and analyzed.

Example 8. A Phase I Open-Label Study to Evaluate the Effect of Olaratumab on the Pharmacokinetics (PK) of Doxorubicin (Dox) in Patients with Advanced Soft Tissue Sarcoma (STS)

Olaratumab (Olara), a fully human monoclonal antibody that selectively binds human platelet-derived growth factor receptor alpha and blocks ligand binding, shows encouraging efficacy in combination with Dox in STS. Patients with metastatic or locally advanced STS not amenable to treatment with surgery or curative radiotherapy, aged years with an ECOG PS of 0-2 and documented LVE fraction ≥50% were included. The primary objective was to assess the effect of Olara on the PK of Dox. Secondary objectives were to further characterize the PK and safety profiles of Olara alone and in combination with Dox. Drug-drug interaction (DDI) was assessed in 21-day cycles, where patients received each drug alone (Cycle 1) then in combination (Cycle 2). In Cycles 3-8, patients with clinical benefit could continue treatment with Olara+Dox. 15-mg/kg Olara was given IV over ~60 min; 75-mg/m$^2$ Dox was given IV over ~15 min. Overall, 25 patients (10 male and 15 female, aged 27-83 years) received at least one dose of study drug; as planned, 15 patients were evaluable for PK and DDI assessment. The AUC and $C_{max}$ for Dox were similar with or without Olara; the 90% CIs for the ratios of geometric LS means for AUC were within the standard no-effect boundary (0.8, 1.25); the 90% CI for $C_{max}$ was only slightly out of the boundary but with a $C_{max}$ ratio close to unity (0.984). After the first infusion of Olara alone (Cycle 1, Day 10), a mean Olara $C_{max}$ of 293 µg/mL was achieved at ~2 h post start of infusion, with a mean $t_{1/2}$ of ~157 h. The mean Olara CL was 0.0259 L/h. After the second infusion (Cycle 2, Day 1, Olara+Dox), Olara serum concentration had a median $t_{max}$ of ~2.8 h post start of infusion, and the mean $C_{max}$ was higher (393 µg/mL), due to the residual Olara serum concentrations from cycle 1. The mean $t_{1/2}$ (~131 h) and CL (0.0218 L/h) were, however, similar to those obtained after the first infusion. These Olara PK results are consistent with those previously reported. No deaths occurred. The most common treatment-emergent AE reported during the study were nausea (48%) and fatigue (44%). One Grade 4 IRR was observed; there was no evidence of QT prolongation. IV infusion of Olara did not have a clinically relevant effect on systemic exposure to Dox when both agents were given in combination. The PK of Olara alone and with Dox was consistent with previously reported data. Olara+Dox had an acceptable safety profile.

What is claimed is:

1. A method of treating a human subject with cancer wherein the cancer is synovial sarcoma, the method comprising:
    a) determining the amount of ME1 nucleic acid or ME1 protein in a cancer cell from a biological sample obtained from the subject; wherein the biological sample is selected from the group consisting of a tissue biopsy or a biological fluid
    b) comparing the amount of ME1 nucleic acid or ME1 protein to a reference value, wherein when the amount of ME1 nucleic acid or ME1 protein is absent, zero or near zero the subject is determined to be responsive to treatment with an inducer of ferroptosis; and
    c) treating the responsive subject as determined in step b) with the inducer of ferroptosis.

2. The method of claim 1, wherein the subject has been previously diagnosed with cancer.

3. The method of claim 1, wherein the biological sample is a tissue biopsy.

4. The method of claim 1, wherein the biological sample is a biological fluid selected from the group consisting of blood, plasma, and serum.

5. The method of claim 1, wherein the inducer of ferroptosis is selected from the group consisting of erastin, RSL3, RSL5, FIN, DPI7, buthionine sulfoximine, acetaminophen, sulfasalazine, sorafenib, artesunate, lanperisone, piperazine erastin, and 1S,3R-RSL3.

6. The method of claim 5, wherein the inducer of ferroptosis is an erastin or an analogue thereof.

7. The method of claim 6, wherein the erastin or erastin analogue is conjugated to a sigma-2 ligand.

8. The method of claim 7, wherein the sigma-erastin compound is SWV-49.

9. The method of claim 1, further comprising treatment with radiation, surgery, chemotherapy and/or targeted therapy.

10. A method for selecting human patients or a patient population having a cancer for a clinical trial wherein the cancer is synovial sarcoma, steps comprising:
    a) determining the amount of ME1 nucleic acid or ME1 protein in a cancer cell from a biological sample obtained from the prospective patient, wherein the biological sample is selected from the group consisting of a tissue biopsy or a biological fluid;
    b) determining the likelihood that a patient is a good candidate for the clinical trial based on the presence, absence or level of ME1 nucleic acid or ME1 protein relative to a reference value, wherein the absence or level of ME1 is correlated with success in a clinical trial; and
    c) administering a therapeutic agent to one or more of the patients determined to be a good candidate for the clinical trial as determined in step b).

11. The method of claim 10, wherein the absence, zero or near zero of ME1 nucleic acid or ME1 protein in the cancer cell of the perspective patient indicates the likelihood that patient is a good candidate for the clinical trial.

12. The method of claim 10, wherein the clinical trial is for an inducer of ferroptosis selected from the group consisting of erastin, RSL3, RSL5, FIN, DPI7, buthionine sulfoximine, acetaminophen, sulfasalazine, sorafenib, artesunate, lanperisone, piperazine erastin, and 1S,3R-RSL3.

13. The method of claim 12, wherein the inducer of ferroptosis is an erastin or an analogue thereof.

\* \* \* \* \*

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 1
gcgcgatcac atggtcctgc t                                             21

<210> SEQ ID NO 2
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 2
ggattcagta atgcaacgtt tcagt                                         25

<210> SEQ ID NO 3
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 3
gccctgaagc agttcgaaat a                                             21
```